United States Patent
McLaren et al.

(10) Patent No.: US 8,850,533 B2
(45) Date of Patent: Sep. 30, 2014

(54) MULTI-LEVEL AUTHENTICATION FOR MEDICAL DATA ACCESS

(75) Inventors: Jeffrey Lee McLaren, Nashville, TN (US); William Dyer Rodes, II, Nashville, TN (US); John Malcolm Toups, Chapel Hill, NC (US)

(73) Assignee: Medaxion, LLC, Nashville, TN (US)

( * ) Notice: Subject to any disclaimer, the term of this patent is extended or adjusted under 35 U.S.C. 154(b) by 851 days.

(21) Appl. No.: 12/789,900

(22) Filed: May 28, 2010

(65) Prior Publication Data

US 2010/0306858 A1 Dec. 2, 2010

Related U.S. Application Data

(60) Provisional application No. 61/182,686, filed on May 29, 2009.

(51) Int. Cl.
| | |
|---|---|
| *G06F 21/00* | (2013.01) |
| *G06Q 50/22* | (2012.01) |
| *G06F 19/00* | (2011.01) |
| *G06Q 50/24* | (2012.01) |
| *G06Q 10/06* | (2012.01) |

(52) U.S. Cl.
CPC .............. *G06Q 50/22* (2013.01); *G06F 19/322* (2013.01); *G06Q 50/24* (2013.01); *G06F 19/327* (2013.01); *G06Q 10/06* (2013.01)
USPC ............ 726/5; 705/2; 705/3; 726/16; 726/17; 726/18

(58) Field of Classification Search
USPC ........................................................ 705/2, 3
See application file for complete search history.

(56) References Cited

U.S. PATENT DOCUMENTS

| 7,346,658 B2 * | 3/2008 | Simpson ........................ 709/205 |
|---|---|---|
| 7,542,911 B2 | 6/2009 | Barret et al. |
| 7,627,334 B2 | 12/2009 | Cohen et al. |
| 7,848,935 B2 | 12/2010 | Gotlib et al. |
| 8,005,947 B2 | 8/2011 | Morris et al. |
| 2003/0069759 A1 | 4/2003 | Smith |
| 2005/0021369 A1 | 1/2005 | Cohen et al. |
| 2005/0033603 A1 | 2/2005 | Suzuki et al. |
| 2005/0055246 A1 | 3/2005 | Simon |
| 2005/0216252 A1 * | 9/2005 | Schoenbach et al. ............. 704/3 |
| 2006/0149589 A1 | 7/2006 | Wager |
| 2006/0195484 A1 | 8/2006 | Mahesh et al. |
| 2007/0073555 A1 | 3/2007 | Buist |
| 2007/0168223 A1 | 7/2007 | Fors et al. |
| 2007/0192133 A1 * | 8/2007 | Morgan ............................ 705/2 |
| 2007/0192137 A1 * | 8/2007 | Ombrellaro ...................... 705/2 |

(Continued)

OTHER PUBLICATIONS

*USPTO Office Action* for U.S. Appl. No. 12/789,783, in the name of Jeffrey Lee McLaren et al., 15 pages, Jan. 30, 2012.

(Continued)

*Primary Examiner* — Jeffrey Pwu
*Assistant Examiner* — Helai Salehi
(74) *Attorney, Agent, or Firm* — Baker Botts L.L.P.

(57) ABSTRACT

Techniques for multi-level authentication for medical data access are supported. A system may include a central medical information management system that provides restricted access to medical data. An accessing device supports multiple different authentication levels. For example, the accessing device may use a combination of device identifiers, passwords, and quick access codes to ensure access only by authorized users.

21 Claims, 10 Drawing Sheets

(56) References Cited

U.S. PATENT DOCUMENTS

| | | | |
|---|---|---|---|
| 2007/0233524 A1 | 10/2007 | Alban et al. | |
| 2008/0154646 A1 | 6/2008 | Barrett et al. | |
| 2008/0184360 A1* | 7/2008 | Kornilovsky et al. | 726/17 |
| 2009/0241184 A1* | 9/2009 | Doering | 726/18 |
| 2010/0286997 A1* | 11/2010 | Srinivasan | 705/2 |
| 2010/0305970 A1 | 12/2010 | McLaren et al. | |
| 2010/0305971 A1 | 12/2010 | McLaren et al. | |
| 2010/0305972 A1 | 12/2010 | McLaren et al. | |
| 2010/0305973 A1 | 12/2010 | McLaren et al. | |

OTHER PUBLICATIONS

*USPTO Office Action* for U.S. Appl. No. 12/790,011, in the name of Jeffrey Lee McLaren et al., 15 pages, Mar. 15, 2012.

*USPTO Office Action* for U.S. Appl. No. 12/789,858, in the name of Jeffrey Lee McLaren et al., 15 pages, Mar. 19, 2012.

*USPTO Office Action* for U.S. Appl. No. 12/789,962, in the name of Jeffrey Lee McLaren et al., 12 pages, Dec. 8, 2011.

Cormac Driver et al., "Facilitating Dynamic Schedules for Healthcare Professionals," © 2007, *IEEE*, 2007.

Elizabeth S. Chen et al., "PalmCIS: a Wireless Handheld Application for Satisfying Clinician Information Needs," *Journal of the American Medical Information Association*, vol. 11, No. 1, Jan./Feb. 2004.

Eneida A. Mendonça et al., "Approach to Mobile Information and Communication for Health Care," *International Journal of Medical Information* (2004) 73, 631-638, 2004.

"Telergy Innovative Nurse Call Features for Healthcare Facilities," *GE Healthcare*, © 2009.

Marcela D. Rodríguez et al., "Location-Aware Access to Hospital Information and Services," *IEEE Transactions on Information Technology in Homemedicine*, vol. 8, No. 4, Dec. 2004.

\* cited by examiner

Washington, George
Case Summary

1102 { ◄ Board | Prep/Assist | Sprvise Direct | Provide Care

1104 {

| | |
|---|---|
| Patient | Washington, George X. |
| Procedure | Tonsillectomy |
| Surgeon | Feelgood J |
| Anesth Sprvisor | Clinton W |
| Anesth Mgr | Gore A |
| OR | 12 @ 12:30, Nov 22, 2008 |
| Id-Case | 123-456-789 |
| Anesthetic | General; ASA = 1 |
| CPT | 91234 Tonsillectomy |
| ICD9 | 45678 Tonsillitis |
| Age | 69 yrs; DOB = Feb 22, 1732 |

| | |
|---|---|
| Prep Start | 12:30 |
| Prep Stop | 12:45 |
| Anesthetic Start | 13:10 |
|     OR Enter | 13:15 |
|         Antibiotic Admin | 13:20 |
|         Intubation | 13:25 |
|         Surgery Start | 13:35 |

Lines

*FIG. 11*

MULTI-LEVEL AUTHENTICATION FOR MEDICAL DATA ACCESS

RELATED APPLICATIONS

This application claims the benefit under 35 U.S.C. §119(e) of U.S. Provisional Application Ser. No. 61/182,686 filed May 29, 2009.

TECHNICAL FIELD OF THE INVENTION

The present invention relates generally to managing medical data, and more specifically to managing medical case and chronology information for one or more medical practices.

BACKGROUND OF THE INVENTION

Many medical care establishments use and share medical case information between medical professionals. For this purpose, medical professionals may use various physical files, written displays, and electronic systems. For example, many anesthesia care locations use a white board to track patients being treated. Many medical professionals also document progress through medical procedures using forms or other paperwork. Such documentation may be used to record events during patient treatment and generate invoices.

SUMMARY OF THE INVENTION

In accordance with the present disclosure, an apparatus, system, and method for implementing multi-level authentication for medical data access is provided which substantially eliminates or reduces disadvantages and problems associated with previous systems and methods.

According to a particular embodiment, a handheld apparatus is provided, which includes a user interface having a display and capable of receiving user input, a wireless network interface coupled to a central medical information management system, a memory for maintaining a medical information management application, and a processor capable of executing the medical information management application. When executed, the medical information management application can communicate a practice key identifying a medical practice to the medical information management system, receive a list of authorized users for the selected medical practice from the medical information management system, display the list using the display, receive a selection of one of the authorized users using the user interface, receive a password using the user interface, communicate the selected authorized user and the password to the medical information management system, and receive a quick access code associated with the selected authorized user from the medical information management system. In addition, the application can receive electronic medical case information corresponding to the selected medical practice from the medical information management system, provide a use mode and a standby mode, where the use mode permits access to the electronic medical case information and the standby mode restricts access to the electronic medical case information. The application can further permit transition from the standby mode to the use mode based on entry of the quick access code using the user interface.

Particular embodiments provide various technical advantages. These techniques provide wide-spread sharing of case information between medical professionals of an anesthesia, surgical or other medical team without requiring medical professionals to use a common physical case board. In addition, techniques of the present disclosure provide updates to case status as they occur, at or near the time of corresponding changes in the field. Moreover, case supervisors or other managers no longer need to check a physical case board or physical location (such as a holding room or operating room) to determine case status.

Particular embodiments provide wide-spread access to medical event data, such as anesthetic or surgical events, thereby sharing information that would otherwise be limited to the few people with physical access to a corresponding paper form for the medical event. Such techniques may also facilitate proactive medical, resource, and manpower management. These techniques may also enable simultaneous access by other team professionals who may be spread throughout a particular location or even at other remote locations.

Particular embodiments provide case status alerting. These techniques facilitate targeted case status alerting that requires neither a callback nor the multicast of alert messages to all medical professionals. Such techniques also facilitate automatic case status alerting without any requirement that the user actively request case status. Thus, important case status information can be sent to appropriate medical professionals allowing them to take appropriate action, such as making a necessary physical location visit.

Particular embodiments may facilitate secure authentication and login to a medical information management system. Techniques for secure login can maintain secure access procedures while eliminating or substantially reducing the use of long usernames and passwords that introduce delay and complexity to those seeking access to the system using a mobile device that may have constrained user input capabilities. Such secure login techniques also provide authenticated access to medical professionals through external networks not located at a health care facility.

Particular embodiments may facilitate the entry of patient and case data items. These techniques allow checklist data to be immediately searchable through appropriate information systems. Such techniques also eliminate transcription error associated with paper-based patient and case data and alleviate possible legibility issues. Additionally, these techniques facilitate the automatic entry of related case items and/or identify data elements that are in conflict. Moreover, such techniques can present or record data elements that may have been overlooked by a medical professional but were appropriate for the medical care rendered.

Particular embodiments may facilitate assuming case roles and handing-off case roles between medical professionals. These techniques accurately record the time associated with case roles and case role-handoff. Such techniques may further enable case roles and any subsequent changes to case roles to be communicated to all medical professionals of a team, thereby eliminating confusion and any patient care difficulties.

Other technical advantages of the present invention will be readily apparent to one skilled in the art from the following figures, descriptions, and claims. Moreover, while specific advantages have been enumerated above, various embodiments may include all, some, or none of the enumerated advantages.

BRIEF DESCRIPTION OF THE DRAWINGS

FIG. 11 illustrates an example case summary interface for summarizing case details and facilitating role-handoffs between medical professionals using a medical information management system.

DETAILED DESCRIPTION OF THE DRAWINGS

Figure 1:
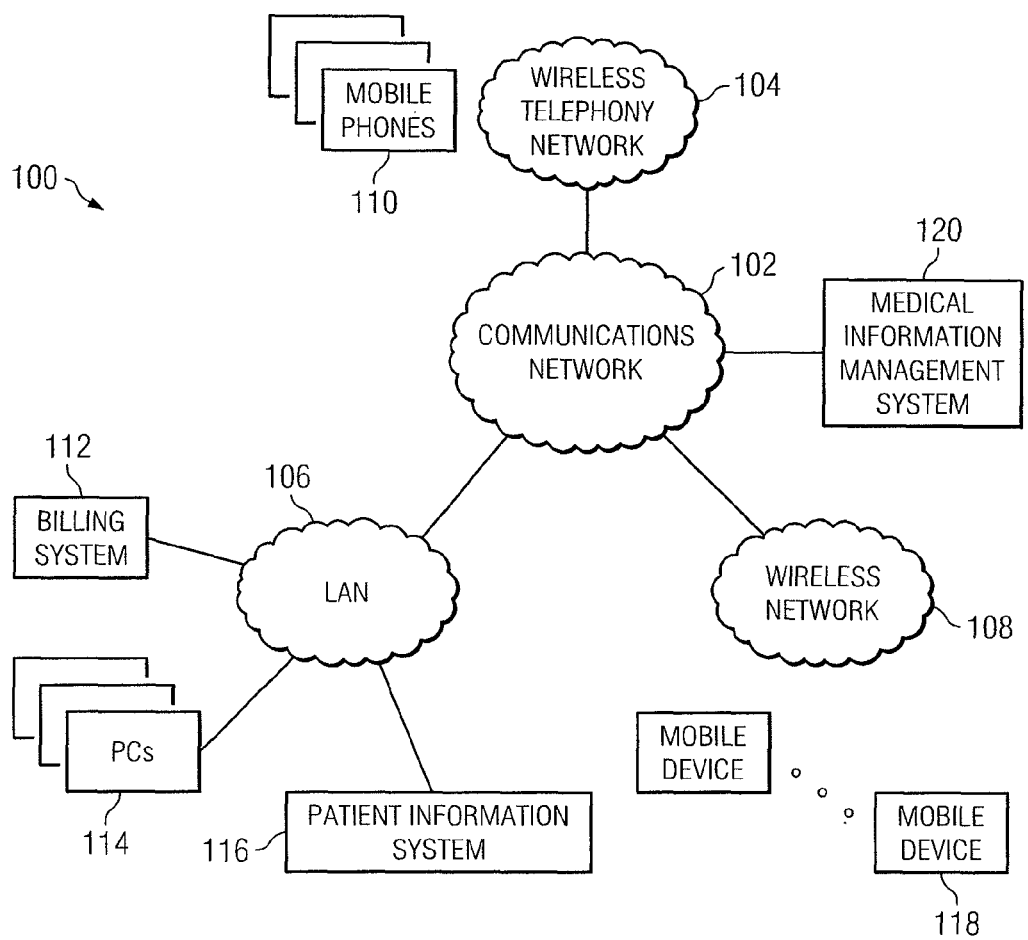
FIG. 1 is a block diagram illustrating a system environment with elements that interoperate to manage and display medical case information.

FIG. 1 is a block diagram illustrating a system 100 with elements that interoperate to manage and display medical case information. The elements of system 100 can support a number of different operations, including maintaining a central, unified repository of patient and case information for one or more practices, facilitating maintenance and display of a graphical case board, enabling entry and display of patient treatment records including case chronology information, facilitating case status alerting in conjunction with tracked medical cases, providing an intuitive graphical user interface for interacting with the system, facilitating entry of medical case information, enabling electronic tracking of medical case assignments and roles in addition to techniques for assuming new assignments and roles and passing assignments and roles between users, and establishing secure authentication and access techniques to facilitate medical case information management functions.

Medical professionals can use the medical information and functionality of system 100 to manage one or more cases for a particular medical practice with one or more practice locations. Users of system 100 can include medical professionals and associated staff, such as surgeons, anesthesiologists, other physicians, certified registered nurse anesthetists (CRNAs), hospital management, billing personnel, medical record managers, and any other medical staff. Under appropriate circumstances, system 100 may further provide patients access to selected information. According to particular embodiments, system 100 may be used to manage information for one or more medical practices. A medical practice is any organization of associated medical professionals and associated personnel, such as a group of doctors and support staff with a common specialty that potentially practice at one or more different practice locations, a group of doctors and support staff associated with a particular hospital, or any other suitable organization of medical professionals. For example, an anesthesia practice may include anesthesiologists, CRNAs, and other support staff that practice at a set of particular medical treatment facilities.

In the illustrated embodiment, system 100 includes a number of elements interconnected by various networks, including a communications network 102, a wireless telephony network 104, a local area network 106, and a wireless network 108. Networks 102, 104, 106, and 108 represent communications equipment, including hardware and any appropriate controlling logic, for interconnecting elements and facilitating communication between these elements. Communications network 102 may include local area networks (LANs), metropolitan area networks (MANs), wide area networks (WANs), any other public or private network, local, regional, or global communication network, enterprise intranet, other suitable wireline or wireless communication link, or any combination thereof. Communications network 102 may include any combination of gateways, routers, hubs, switches, access points, base stations, and any other hardware, software, or a combination of the preceding that may implement any suitable protocol. For illustrative purposes, system 100 is also shown as including other specific types of networks, including wireless telephony network 104, local area network 106, and wireless network 108. The use of these or similar networks facilitate seamless communication between components of system 100 regardless of their geographic location or communication protocols.

As illustrated, system 100 includes a wireless telephony network 104 coupled to communications network 102. Wireless telephony network 104 represents communications equipment, including hardware and any appropriate controlling logic, for interconnecting elements and facilitating communications by wireless devices. Wireless telephony network 104 may include gateways, call managers, routers, hubs, switches, access points, base stations, cellular towers, radio networks, satellite telephone equipment implementing appropriate protocols for wireless telephony communications. While only one wireless telephony network 104 has been illustrated, it should be understood that various embodiments may operate using more than one wireless telephony network. In addition, various embodiments may incorporate wireless telephony networks 104 in other networks of system 100 such as, for example, wireless network 108.

The illustrated embodiment of system 100 also includes a local area network 106 coupled to communications network 102. Local area network 106 represents communications equipment, including hardware and any appropriate controlling logic, for interconnecting elements within a limited network area (as compared with, for example, wide area networks). Local area network 106 may include any combination of gateways, routers, hubs, switches, access points, base stations, and any other hardware, software or combination thereof using suitable protocols to support communications. For example, local area network 106 may be the established network infrastructure deployed at a particular hospital or other medical facility. While only one local area network 106 has been illustrated, it should be understood that various embodiments may operate using multiple local area networks 106. In addition, various embodiments may incorporate local area networks 106 in other networks of system 100.

System 100 also includes wireless network 108 coupled to communications network 102. Wireless network 108 represents communications equipment, including hardware and any appropriate controlling logic, for wirelessly interconnecting elements and facilitating communication between other elements of system 100. For example, wireless network 108 may operate according to one or more of the 802.11 standards promulgated by the Institute of Electrical and Electronic Engineers (IEEE). Wireless network 108 may include any combination of gateways, routers, hubs, switches, access points, base stations, wireless telephone systems and any other hardware, software, or combination thereof. While only one wireless network 108 has been illustrated, it should be understood that various embodiments may operate using multiple wireless networks 108. In addition, various embodiments may incorporate wireless networks 108 in other networks of communications network 102.

These networks interconnect other elements of system 100, including mobile phones 110, a billing system 112, personal computers (PCs) 114, patient information system 116, mobile devices 118, and a medical information management system 120. It should be understood that while system 100 is illustrated as including specific types of networks, various embodiments may operate using any suitable arrangement and collection of networks that enable appropriate communications.

Mobile phones 110 represent portable hardware and appropriate controlling logic for providing telephony and/or advanced data services. For example, mobile phones 110 may support voice and data communications. Mobile phones 110 may include smart phones capable of transmitting and receiving multiple forms of media including but not limited to still audio, text messages, video, images, and content from disparate services. As illustrated, mobile phones 110 may be coupled to wireless telephony network 104 and capable of communicating to other components of system 100. According to particular embodiments, system 100 may use mobile phones to provide alerts or other information to medical personnel.

Billing system 112 represents hardware, appropriate controlling logic, and data associated with billing for medical services. For example, billing system 112 may be a computer server designed to manage billing for a particular medical practice, such as an anesthesia practice. Billing system 112 may be network accessible to facilitate communication with other elements of system 100.

Personal computers (PCs) 114 represent general-purpose computers, including appropriate hardware, controlling logic, and data that may be used to interface with other system components such as billing system 112, patient information system 116, mobile devices 118, and medical information management system 120. For example, PCs 114 may be workstations, laptops, netbooks, tablet computers, personal data assistants (PDAs), or any other suitable computing device. PCs 114 may support a wide variety of operations such as web browsing, word processing, and managing business data. According to particular embodiments, PCs 114 provide access, potentially through web-based interfaces, to information managed by other elements.

Patient information system 116 represents suitable hardware components, controlling logic, and data for managing patient information, such as patient demographic information, medical histories, and/or other relevant medical information such as practice employees and work schedules. For instance, patient information system 116 may be embodied in a computer system or a network of computers, which are capable of maintaining patient information such as patient identifiers, case identifiers, surgery types, date-of-birth, surgery schedule, operating room, attending surgeon and/or anesthesiologist, insurance information, medical history, and other patient-specific information as appropriate for various aspects of a medical practice. Some embodiments of the present disclosure may include a patient information system 116 deployed at a medical practice or other medical care facility, while other embodiments may include a global patient information system 116 for maintaining patient information. As illustrated, patient information system 116 may be coupled to a network, such as local area network 106, to facilitate communication to other elements of system 100. While only one patient information system 116 is shown, it should be understood that various embodiments may include multiple appropriately deployed patient information systems 116.

Mobile devices 118 represent any suitable portable hardware, including appropriate controlling logic and data, capable of communicating with remote devices to facilitate management of medical information. For example, mobile devices 118 may include, but are not necessarily limited to, mobile telephones, advanced ("smart") phones, personal digital assistants (PDAs), wireless handsets, notebook computer systems, and tablet computer systems. According to particular embodiments, mobile devices 118 include wireless devices with advanced user interfaces, such as the APPLE iPhone, iPod Touch, or iPad.

Medical information management system 120 represents any appropriate combination of hardware, controlling logic, and data for managing medical information and supporting interactive access to that data from multiple remote (and potentially highly mobile) devices. For example, medical information management system 120 may include a networked server or collection of networked servers, or could include in one or more virtual servers capable of acquiring computing resources on-demand depending on the dynamically determined needs of the system. Using virtual servers, medical information management system 120 could be scaled dynamically based on system requirements and real-time usage, without limiting operation to a particular physical computer server having fixed computing resources. This could facilitate the scalability, efficient operation, high availability, and cost effectiveness of the system. As illustrated, medical information management system 120 couples to networks, such as communications network 102, to facilitate communication to other elements of system 100.

Particular embodiments are designed to operate in a network environment that facilitates the retrieval and presentation of medical data to end users, facilitating real-time tracking of medical professional activity related to the provision of patient care (events tracked at or near in time to the actual provision of patient care) provided at a medical facility such as a hospital or other medical care establishment. Systems, methods, and software exemplified in the present disclosure may increase the coordination of patient care, enhance the reliability of medical information, and help ensure the accuracy of medical record keeping and billing.

In operation, elements of system 100 operate together to perform various medical information management functions including but not limited to maintaining a central, unified repository of patient and case information for one or more practices, facilitating maintenance and display of a graphical case board, enabling entry and display of medical professional activity information and patient treatment information having case chronology information, facilitating case status alerting in conjunction with tracked medical cases, providing an intuitive graphical user interface for interacting with the system, facilitating entry of medical case information, enabling electronic tracking of medical case assignments and roles in addition to techniques for assuming new assignments and roles and passing assignments and roles between users, and establishing secure authentication and access techniques to facilitate ease-of-use and other medical case information management functions.

For example, medical information management system 120 is capable of maintaining a central, unified repository of patient, medical professional activity, and case information for one or more medical practices. For example, medical information management system 120 may maintain patient treatment records that dynamically track care provided to patients for one or more medical practices. Medical information management system 120 can dynamically update this information based on communications with medical personnel using mobile devices 118 (or other suitable access devices). Medical information management system 120 may also access and exchange information with other information management and processing elements of system 100. In particular embodiments, medical information management system 120 acquires patient management information from one or more patient information systems 116. For example, medical information management system 120 can upload patient information for all patients scheduled for treatment on a particular day.

Medical information management system 120 maintains information on patients and medical professional activity and supports interactions with other devices to manage and display the medical and logistics information. For instance, mobile devices 118 can access medical information management system 120 to download information for display in the form of a graphical case board showing all cases mapping to a particular medical practice or even a particular location for a medical practice. In certain implementations, mobile devices 118 may present the medical case board information in tabbed interfaces with tabs corresponding to predefined phases of care for a medical practice. Mobile devices 118 could further interface with medical information management system 120 to receive and manage more detailed patient treatment information through other specialized interfaces, such as a case summary interface for summarizing information for a case or a case details interface for detailing the chronology and other medical events associated with a case. For example, mobile devices 118 may present a graphical user interface showing patient treatment records in tabbed interfaces with the ability to list medical events for real-time tracking of cases. Users of mobile devices 118 can use these interfaces to provide real-time entry of information corresponding to treatment events, which medical information management system 120 can then use to update the case board and progress patients through phases of treatment. This type of process uses the capture of treatment information (such as billable events or other required records) to feed other processes that, in typical systems, require separate efforts to track, such as a case white board that requires case board runners to physically update.

Particular embodiments support secure access to medical information management system 120 using an access scheme designed to maintain a high level of security while supporting user-friendly access with devices that may have limited or non-traditional user interfaces. The access techniques may use a combination of authorization information checked in one or more steps, such as a username, password, quick access code (such as a personal identification number (PIN) or other string of characters or gestures), secure hash, device identifiers, or other secure authentication information. In certain embodiments, secure authentication is a multi-step process that uses different types of information provided at different stages of access. According to particular embodiments, one step may involve device identification. For example, a particular mobile device 118 may have a secure device hash or other suitable unique identifier that can be registered with and verified by medical information management system 120. Another step may involve a secure token or key that uniquely maps to a particular medical practice (which may use information from other steps, such as a secure device hash that links a specific mobile device 118 to a particular medical practice). Another step may involve providing a user name and associated password, for example, by selecting a user name from a list of available users and then providing a password that meets certain length and character requirements. Another step may require entry of a quick access code, such as a four or six number pin or a particular pre-recorded gesture. These different steps and secure authentication information may be combined and used at particular times to ensure that access to medical information is suitably restricted while allowing authorized users of mobile devices 118 relatively easy access to information. For example, after requiring one or more relatively high-security authentication steps, subsequent access over the course of some period of time may only require a subset of credentials, such as a quick access code. During that period of time, mobile device 118 could enter sleep modes or other application and, upon a user wishing to restart access to medical information, mobile device 118 would simply require reentry of the quick access code. If mobile device 118 were restarted or some extended period of time passed, system 100 could require reprocessing through one or more of the higher security steps.

After access is granted, the user may select a practice location from a list of available practice locations for the medical practice and thereby gain access to the corresponding medical case information and functionality of the system. Following authentication, mobile devices 118 and medical information management system 120 may interoperate to present medical information in an intuitive graphical case board interface to the user. For example, the graphical case board may enable entry and display of a patient treatment record including case chronology, case status alerting in conjunction with tracked medical cases, electronic tracking of medical case assignments and roles, assuming new assignments and roles, and passing assignments and roles between users.

The graphical user interface allows medical professional activity, case board information, and patient treatment records to be securely accessed and displayed. In addition, this information can be used to track billing-related events as a patient progresses through various medical events or sub-events of a particular surgery or other medical procedure. For example, mobile devices 118 may securely present a graphical case board to view the status of a patient scheduled for a medical procedure, where medical information management system 120 actually maintains all of this information. Similarly, PCs 114 may securely access medical information management system 120 to view similar information. Thus, for instance, an interface available at PCs 114 may display patient information or medical events maintained by medical information management system 120, portions of which may be indirectly derived from other components of system 100 such as patient information system 116 or one or more mobile devices 118.

In addition to viewing medical case board information in a graphical case board interface, embodiments of the present disclosure facilitate the presentation and tracking of patient treatment records for particular cases. A patient treatment record represents any collection of information (or subset of that information) detailing information about a patient and the patients case(s). For example, a patient treatment record could include general demographic information for the patient (name, age, medical history, etc.) and case specific information, such as assigned or current treatment rooms (e.g., and assigned operating room), a chronology of treatment events, codes, involvement by specific medical personnel, notes, and other suitable case information.

A patient treatment record may be accessed to display a graphical representation of a sequence of steps or medical events corresponding to the chronology of a medical procedure for a particular case. For this purpose, a patient treatment record may include a time record associated with each step or medical event corresponding to a case chronology. Thus, medical personnel may view and track billing-related events such as the performance of a step in a medical procedure. For example, an anesthesiologist may track the time spent attending to a patient or administering anesthesia by recording anesthesia start and stop using a graphical user interface on mobile devices 118. The entry of these events can feed other aspects of the system, such as the tracking of patients on electronic case boards.

System 100 may also use a set of case checklist items and patient information to track cases, including non-time specific billing information, procedure and diagnostic codes, and information on general quality of care rendered by one or more medical professionals. In a similar fashion, other events and checklists may be incorporated into the graphical user interface to implement a set of institutional policies and procedures for delivering patient care as required at a particular medical practice or facility. The listed medical events and case checklist items can be based on customized templates, potentially customized for individual practice locations, such as for a specific hospital.

In addition to tracking medical cases, embodiments of the present disclosure may use medical information from medical information management system 120 to manage medical case assignments and roles among a team of medical professionals. For example, a medical professional may use features provided in a graphical user interface on mobile device 118 to handoff or take over a medical role. In an anesthesia setting, this may involve a first CRNA who is actively providing care for a patient handing-off this management role to a second CRNA when the first CRNA requires a break. Another example may include an anesthesiologist who is supervising multiple CRNAs handing-off his supervisory role to another anesthesiologist when he can no longer act in that capacity. In particular implementations, the role-handoff process may require that the relieving party initiate the role-handoff process to take-over a case role from another medical professional. Moreover, this role-handoff process may work within constraints established by institutional policies and procedures for a particular facility or collection of facilities. For example, supervising anesthesiologists may be prohibited from relieving other anesthesiologists when they are already supervising a maximum of four CRNAs. Similarly, CRNAs may be prohibited from relieving other CRNAs when they are already providing care for another patient. Medical information management system 120 may maintain a set of role handling rules that define permitted roles for classes of medical personnel, limits on those roles (e.g., only supervise up to four cases, and not while performing any procedure), and details for how handoffs must be processed and verified.

System 100 may further provide case alerting functionality that enables targeted messaging to appropriate medical professionals using a variety of communication techniques and protocols. Case alerts may occur automatically or may be user-initiated. Additionally, case alerts may take on a variety of forms including voice, text, multimedia, or application specific (e.g., embedded notification in a customer medical information management application running on mobile devices 118). In the case of automatic notifications, case alerting schemes may deliver alerts or notifications on the occurrence of some predefined case event. Case alerts can be sent to a variety of individuals and can based on various roles including medical case role, team management role, or context-based role such as those who respond to specific clinical changes In one example, supervising anesthesiologists may be alerted on their corresponding mobile device 118 by medical information management system 120 when a particular event occurs for a case for which they are responsible. Another case alert may involve supervising anesthesiologists being alerted when a patient transitions from one predefined phase of care to another, such as from a pre-operation phase to intra-operation phase. Case alerts may also be used in conjunction with role-handoffs. For example, medical information management system 120 may notify one or more supervised CRNAs when a role-handoff results in a change to their supervising anesthesiologist.

Case alerts may also be delivered on disparate networks. For example, medical information management system 120 may deliver a case alert message or notification via communications network 102 and wireless telephony network 104 to mobile phones 110. Thus, certain embodiments may allow a medical professional to be notified of changes occurring in the field in the form of voice, text, or multimedia messages even after leaving the associated medical facility. In conjunction with case alerts and notifications, users receiving alerts may confirm delivery and/or issue an appropriate response. Thus, for example, mobile phones 110 may receive a case alert and send one or more responsive messages to medical information management system 120 and/or mobile devices 118 deployed at a particular medical facility through the coordination of medical information management system 120 and networks 104, 102, and 108. Therefore, medical professionals can use case alerts and notifications to stay apprised of real-time changes occurring at a medical facility, assess the requirements for immediate patient care, and coordinate with other medical professionals to respond as medically appropriate.

Elements of system 100 may also facilitate coordination with a billing system 112 to develop invoices and reports. For example, medical information management system 120 may communicate with one or more billing systems 112 to support billing-related functions. Thus, medical information management system 120 can support billing systems 112 to produce appropriate invoices for surgical procedures, anesthesia services and/or other billing-related medical events corresponding to a medical provider site (e.g., a particular hospital or hospital floor) or individual patients. Billing system 112 may then forward invoices or other billing information to the appropriate insurance provider, patient, or other responsible party. Thus, a billing system may be seamlessly integrated with other functionality described in this disclosure to perform various medical billing operations.

While system 100 is illustrated as including specific components arranged in a particular configuration, it should be understood that various embodiments may operate using any suitable arrangement and collection of components capable of providing functionality such as that described.

Figure 2:
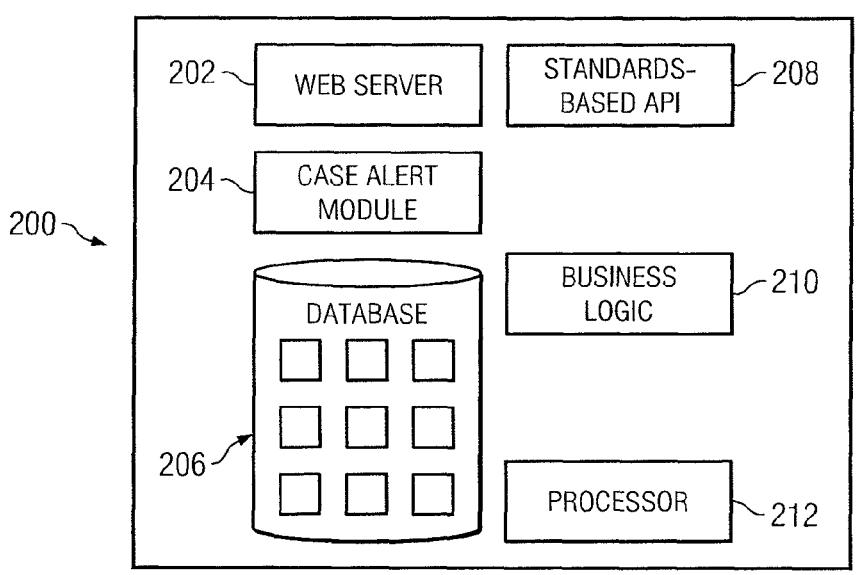
FIG. 2 is a block diagram illustrating an example medical information management system for facilitating management of medical case information.

FIG. 2 is a block diagram illustrating a system 200 representing an example embodiment of medical information management system 120 which has elements that interoperate to facilitate the management of medical case information. The elements of system 200 can support a number of different operations including maintaining a central unified repository of patient and case information for one or more practices, which permits the maintenance of case board information, patient treatment records, and case summary information. The elements of system 200 may also facilitate case status alerting in conjunction with tracked medical cases and the graphical display of a user interface for interacting with the system and the entry of medical case information from one or more devices such as mobile phones 110, PCs 114, and mobile devices 118. In addition, system 200 may facilitate the management of medical case assignments and roles and enable the assumption of new assignments and roles and passing assignments and roles between members of a medical care team. System 200 further is operable to establish secure authentication techniques to facilitate secure access to medical information management functions and data.

System 200 represents any appropriate combination of hardware, controlling logic, and data. For example, system 200 may be one or more computer servers or virtual computer servers capable of providing the appropriate functionality for centrally managing patient and case information for one or more practices. As illustrated, system 200 includes a web server 200, a case alert module 204, a database 206, a standards-based application programming interface (API) 208, business logic 210, and one or more processors 212.

Web server 202 represents any appropriate combination of hardware, controlling logic and data for interfacing with remote devices using web-based protocols to provide web-based access to the medical information and functionality provided by system 200. For example, web server 202 may be a web host that serves web pages to facilitate access to some or all functions of system 200.

Case alert module 204 represents any appropriate combination of hardware, controlling logic, and data for facilitating case status alerting in conjunction with tracked medical cases and activities of a medical care team. In addition, case alert module 204 may be coupled to one or more networks such as a telephone network, a wired or wireless computer networks, a cellular network, a radio network, a satellite network, or any other appropriate network capable of delivering case status alerts.

Database 206 represents any appropriate combination of hardware, controlling logic, and data for maintaining patient information, case information, medical professional activity information, and other system-related data. As illustrated, database 206 has various data components including patient data, case data, user data, practice data, system metadata, location data, device registry data, user access logs, and rules data.

Patient data includes information regarding patients tracked by system 200. For example, for each patient tracked by system 200, database 206 may maintain a patient identifier (such as a name), general demographic information (such as the patient's date-of-birth), and any appropriate responsible party or insurance information.

Case data represents a collection of information corresponding to a particular case associated with a scheduled medical procedure for a patient at a defined medical facility. Such information may include a case identifier or reference, information on a procedure scheduled to occur or currently occurring (such as surgery type), an assigned operating room, the attending physician or anesthesiologist, records of the case chronology of a scheduled medical procedure, various medical events in the case chronology, involvement by specific medical professionals, procedure and diagnostic codes, modifiers, and audit logs corresponding to various medical events entered by specific practice personnel. According to particular embodiments, system 200 updates case data based on real-time inputs from mobile devices 118. System 200 can provide patient treatment records to other devices based on information maintained in patient and case data.

User data represents a collection of information corresponding to various users who interact with system 200, including users of PCs 114, mobile phones 110, and mobile devices 118. Such user information may include authentication data such as authorized users corresponding to a defined practice location, each authorized user's passwords, each authorized user's system access history, each authorized user's usage preferences, and other access codes. This information can be used to provide secure access to system 200 and as appropriate, prohibit unauthorized access to medical information maintained by system 200.

Practice data represents practice wide settings and preferences corresponding to a medical practice and, potentially, for one or more specific practice locations. This may include rules and policies for managing medical data instituted by a particular medical practice. Practice data may also include a core set or subset of medical procedure terminology for a medical practice or procedure. Such medical procedure terminology may conform to Current Procedural Terminology (CPT) or International Classification of Diseases (ICD) codes. Such codes may be used in conjunction with recording billing-related events for a particular practice. Practice data may also include information related to historic utilization and appropriate future allocation of medical professional resources available to the practice. Other information included in practice data may include billing report preferences, billing export preferences, and any translation or transmission settings necessary to communicate various reports to the defined medical practice at a particular location. This information facilitates the generation of billing reports and invoices in the desired format for a practice.

Location data includes information corresponding to a defined practice location, either tied to a particular medical practice at that location or based on rules of information about multiple medical practices that may provide care at that location. Location data may include case chronology templates, checklist templates, quality control templates (such as a physician quality reporting incentives (PQRI) template), and other templates for capturing information in a form customized to a particular practice location or practice location/medical practice specified manner. These templates facilitate the recording of medical events occurring in the field, in addition to facilitating the real-time tracking of quality control measures. For example, a case chronology template may define a set of rules regarding entry of medical events associated with a procedure and include time events or other entries. Case chronology templates may be manually and/or dynamically adjusted based on operations at one or more practice locations, such as based on feedback showing a particular event that consistently must be manually entered at a particular practice location.

Rules data defines permitted or prohibited activities corresponding generally to users, medical professional roles, specific medical practices, locations, medical procedures, or other activities. For example, these rules may implement practice-specific or location-specific policies affecting medical professionals or relevant medical events. For example, a rule for an anesthesia practice may prohibit an anesthesiologist from managing more than four CRNAs. Thus these rules provide guidelines for active case management in terms of a workflow that can be specific to a medical specialty or a medical facility.

Standards-based API 208 represents hardware, appropriate controlling logic, and data for interfacing with remote components using standardized processes and protocols. For example, standards-based API 208 may interface with patient information systems 116 to retrieve patient information from one or more medical practices. As another example, standards-based API 208 may facilitate interactions with remote devices to support alerting functions, such as through text messaging with mobile phones 110.

Business logic 210 represents hardware, controlling logic and data associated that controls the fundamental operation and administration of system 200, including interactions of elements to provide the interactive medical information management processes described herein. For example, business logic 210 may be software for execution by one or more processors to provide a central medical information management service that tracks medical professional activity and patient care, and interfaces with mobile devices 118. Processor 212 represents one or more computer processors for executing business logic 210 or other software or controlling logic associated with elements of system 200.

In operation, elements of system 200 operate together to perform various functions of the present disclosure, including maintaining a central, unified repository of patient and case information for one or more practices and facilitating the maintenance of medical professional activity information, patient treatment information including case chronology, and medical case summary information. System 200 uses this information to support applications on mobile devices 118 that can interface with and graphically present that information. In addition, system 200 facilitates case status alerting for tracked medical cases, providing an intuitive graphical user interface for interacting with the system and enabling the electronic tracking of medical case assignments and roles and medical case role-handoffs between assigned medical professionals. Elements of system 200 can ensure that users of system 200 are securely authenticated prior to accessing medical information and case management functions. Accordingly, only those users who are properly authenticated may interact with system 200.

For example, elements of system 200 are operable to maintain a central, unified repository of patient and case information for one or more medical practices. In particular, processors 212 may execute appropriate business logic 210 to communicate with one or more patient information systems 116 to retrieve patient information corresponding to a medical practice. System 200 stores information in database 206, generates day-of-care information (for example, based on patient information retrieved from one or more patient information systems 116), communicates information from database 206 to computing devices (e.g. mobile phones 110, PCs 114, and/or mobile devices 118), and receives updates, including real-time information, from one or more computing devices. This information can then be used by a graphical user interface to display and facilitate real-time data entry and management of medical case and chronology information. Any changes occurring at these computing devices that are relevant to real-time case management and medical professional coordination may then be received over a network. Accordingly, elements of system 200 interact with one another to actively manage medical case information as patients receive care.

As discussed above, system 200 may impose various authentication requirements before permitting access to functions and information of system 200. These may include one or more levels of interactive authentication steps requiring user interactions as well as ongoing, automated exchanges. For example, each communication or request from a particular mobile device 118 may include a secure device hash identifying that mobile device 118 to system 200.

According to particular embodiments, system 200 implements a multi-level access scheme that requires different types of credentials at each level. For example, system 200 could require a user name and password (potentially in combination with a device hash) for first-level access and then a quick access code for second level access and for re-access over some period of time. System 200 may compare these received values with stored user data according to business logic 210 to determine whether the user identified in the request has appropriate credentials for accessing the medical information and functionality of system 200. Using these secure authentication means, system 200 can guarantee that access to case information and specific patient medical data is appropriately protected.

During operation, system 200 provides medical information, such as case board, medical professional activity, or patient treatment information, for presentation and use by graphical user interfaces presented on mobile devices 118. To support this functionality, system 200 maintains real-time tracking information for patients receiving care, and activities of identified medical professionals, provides the information to mobile devices 118, and receives and processes requests to update the information. For responding to medical case board information requests, case data for multiple cases may be accessed for retrieving a subset of the case details for forwarding to the remote computing device to display on its graphical user interface. For example, in response to a case board request from mobile device 118, system 200 may compile selected information for all patients scheduled to or receiving care at a practice location for a medical practice associated with the requesting mobile device 118 and then provide that information to the requesting mobile device 118, for example, as a collection of patient treatment records.

Mobile devices 118 may also request information or provide updates for particular cases. In response, system 200 may provide responsive patient treatment records that include details of the requested patient and case extracted from database 206 (potentially with more information than for case board requests). The accessed case data may include medical professional activity data relative to the case, procedure information, diagnosis information, case chronology data such as medical events associated with a particular case and any related checklist items. As appropriate, system 200 may log requests or other access events in the access logs of database 206 according to business logic 210 and any corresponding rules maintained in the rules data of database 206.

In responding to information requests, system 200 may process the response information as appropriate based on the requesting computing device. Such processing may include formatting the case board or patient treatment record according to location data in database 206. For example, case board information may be arranged according to a template that may organize all cases for a location into categories corresponding to predefined phases of care defined in the location data for a specific practice. For an anesthesia or other appropriate practice those predefined phases of care may correspond to schedule, pre-operation, intra-operation, and post-operation phases. As another example, aspects of a patient treatment record may be organized according to an event chronology template, a modifier checklist template, and/or a quality control template defined in the location data. Thus, the templates and other information in the location data of database 206 instruct processor 212 and business logic 210 how a practice wishes the requested information to be populated, organized, and delivered for subsequent presentation on a graphical user interface of a requesting computing device. However, some or all of the customization and formatting of information may be handled by other elements, such as mobile devices 118.

In addition to facilitating the display of chronological stages at one or more remote computing devices, system 200 can also receive real-time updates corresponding to specific billing-related events such as the performance of a step in a medical procedure. According to particular embodiments, some or all of these may be "real-time," that is, provided from care-givers as (or very nearly in time to) a patient receiving care indicated by an update. For example, an anesthesiologist may use mobile device 118 to track, in real-time, time spent with a patient or time spent actually administering anesthesia from start to finish. Such durational information may be provided to system 200 and maintained in an appropriate time record of a patient treatment record. Updates may also include specific checklist items corresponding to events having no time value, or policy-based requirements of a medical procedure. Once an update is processed, other computing devices may securely receive case information including these updates in the form of case board information, patient treatment records, case alert, or other appropriate form. In this manner, all medical professionals associated with the case can be kept aware of any changes occurring in real-time for a particular case.

In operation, system 200 may also manage medical case assignments and roles among a set of medical professionals. In particular, a medical case may include multiple roles corresponding to responsibilities of various medical professionals with respect to a specific case. In certain embodiments of the present disclosure, a medical professional may use features provided at their respective computing device to assume a role or handoff a medical role to another medical professional. Such handoffs may be necessary for shift changes, breaks, or for any other number of practical reasons. To facilitate the assumption of roles and role-handoff, system 200 may receive a request to handoff the role from a relieving party. In particular implementations, requiring the relieving party to initiate the role-handoff ensures that a case is not inadvertently abandoned when a role-handoff is not successful. For example, if the party seeking relief from a case were to initiate the role-handoff, a situation may arise where the relieving party refuses to accept the role or is otherwise unable to accept the role and the case may be abandoned altogether. If, however, the relieving party were required to initiate the role-handoff process, the role for that case continues to remain assigned to the party seeking relief until the role-handoff is in fact successful.

In response to a role assumption or role-handoff request, system 200 may access rules data found in database 206 to determine whether the role change is permitted for this particular practice. Checking against such rules ensures that policies specific to a medical specialty or facility are properly implemented. For example, as a matter of institutional policy, an anesthesia practice may prohibit the role-handoff of a case from one anesthesiologist to another if the relieving anesthesiologist is already supervising more than four cases as outlined in the rules data of database 206. As with all other events, system 200 may log the requests and subsequent role changes. In some embodiments, system 200 may facilitate role-handoff coordination between medical professionals by seeking appropriate approvals prior to a role-handoff. For example, if a relieving party initiates the role-handoff process, then system 200 may seek approval from the party that would be relieved through a confirmation or other appropriate message. Likewise, if a party seeking relief initiates the role-handoff process, then system 200 may seek similar approval from the relieving party. If a role change is appropriate and finalized, system 200 updates the case data to indicate the successful assumption or role-handoff for the case. This case update can then be accessed by other computing devices and/or systems such that they are made aware of the role-handoff in real-time. In particular implementations, this change in case data may cause computing devices associated with the practice or case to receive a real-time update in the form of case board information, patient treatment record, case alert, or any other appropriate form for receiving case updates.

During operation, system 200 may also provide case alerting functionality to notify medical professionals of relevant medical events or concerns. According to particular design considerations, case alerts may be automatically generated or user-initiated. For automatic case alerts, system 200 is operable to maintain a list of customizable events for which a case alert should be issued. In particular, database 206 may include a set of alert rules specifying alerts, rules for triggering an alert (such as occurrence of a particular event), and alert execution information (such as contact information and procedures for handling a triggered alert). Subsequent events, such as updates to case data can then trigger case alerts. For example, an event trigger may require all role-handoffs for a case to notify the party being relieved and/or supervising medical personnel. Once an event trigger is associated with a medical event in the case data, subsequent events matching the event trigger can cause the case alert module 204 to notify the medical professional indicated in the event trigger in the form of a case alert.

Case alert module 204 may send a alert messages using any appropriate formats and protocols, including voice, text, or multimedia messages, based on the targeted device. As discussed, the form and network for delivering a case alert may be defined by the contact information of the event trigger. For example, the contact information may indicate that a supervising medical professional wishes to be notified of relevant role-handoffs in the form of a text message using a short message service (SMS) network. In certain implementations, case alert system 204 may support interactive case alerts. For example, in addition to notifying particular medical professionals of successful role-handoffs, case alert module 204 may facilitate the role-handoff process by allowing medical professionals to accept, decline, and confirm role-handoffs. Accordingly, embodiments of the present disclosure support configuring, sending, and receiving automatic case alerts for communicating medical events to medical professionals.

Case alert module 204 can also process user-initiated messages. For example, a user of a particular mobile device 118 may choose to alert other users to a particular event or information. Once the case alert module 204 receives this user-initiated message, case alert module 204 can determine how, when, and where to send the message based on the received message and intended recipient. In a similar manner, case alert module 204 can also receive responses to user-initiated messages and forward them to the intended computing devices. User-initiated messages may be sent in any suitable form and using any appropriate network. For example, the messages may be a text, voice, or multimedia message sent over a wired, wireless, cellular, or any other network. Thus, system 200 allows medical professionals to stay apprised of real-time changes to case information and communicate with each other efficiently to assess the requirements of immediate patient care and coordinate effectively with each other.

System 200 may also interact with billing systems such as billing system 112 to develop billing invoices and reports. In particular, upon request or at defined intervals, system 200 may access practice data residing at database 206 that defines report preferences for delivery of billing-related events. In addition, system 200 may access export preferences, and translation and transmission settings for placing reports in appropriate form for delivery to the billing system 112 corresponding to a medical practice. Alternatively, export preferences may define the intended destination of bill reports or invoices. Thus, insurance companies and other responsible parties may receive a bill or an invoice developed according to their predefined report preferences.

While system 200 is illustrated as including specific components, it should be understood that various embodiments may operate using any suitable arrangement and collection of components.

Figure 3:
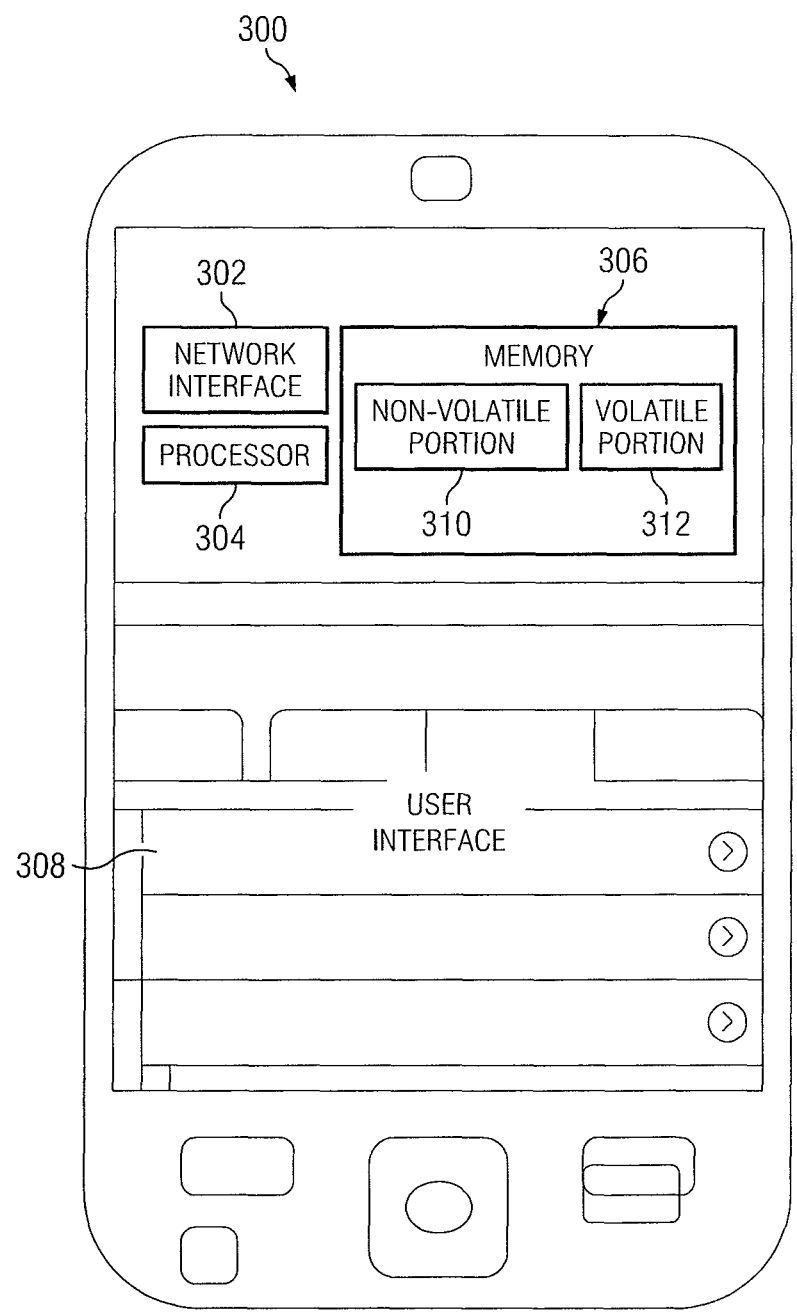
FIG. 3 is a block diagram illustrating an example embodiment of a handheld device for executing a medical information management application for displaying and tracking medical case information.

FIG. 3 is a block diagram illustrating a mobile device 300 representing an example embodiment of mobile device 118. As illustrated, mobile device 300 includes a number of components that operate together to facilitate the management of medical information. Mobile device 300 can support a number of different operations, including receiving practice location and user configuration information, case board information, patient treatment information, and case summary information for presentation and management on a graphical user interface. In addition, mobile device 300 may facilitate case status alerting and tracking medical cases. Mobile device 300 is further operable to facilitate the management of medical case assignments and roles through a graphical user interface. Specifically, the graphical user interface enables assuming assignments and roles and conducting assignment and role-handoffs between users. Additionally, mobile device 300 is capable of securely accessing medical case information from a remote medical information management system using appropriate authentication and secure access techniques.

As illustrated, mobile device 300 includes a number of components for maintaining and displaying medical information. Mobile device 300 may represent any suitable portable hardware, including appropriate controlling logic and data capable of communicating with remote devices and systems, receiving user input, and displaying medical information. As shown, mobile device 300 includes several components, which may include a network interface 302, a processor 304, a memory 306 and a user interface 308. The illustrated embodiment further discloses memory 306 as including a non-volatile portion of memory 310 and a volatile portion of memory 312.

Network interface 302 represents any appropriate combination of hardware and controlling logic for coupling to one or more networks. Network interface 302 may support any number of suitable protocols for communicating on a communication network. For example, network interface 302 may be a wireless local area network interface, cellular network interface, satellite interface, and/or any other appropriate interface for communicating on a communication network. Network interface 302 may have multiple interfaces for handling different communication protocols.

Processor 304 represents one or more processing elements, including hardware, logic, and data capable of controlling the operation of mobile device 300. For example, processor 304 may be a computer processor for executing a medical information management application stored in memory 306, or any other software or controlling logic associated with mobile device 300, such as a mobile operating system.

Memory 306 represents appropriate hardware and control logic for maintaining a medical information management application and case information corresponding to one or more medical practices. Memory 306 may also include storage for other data, such as a mobile operating system of mobile device 300. As illustrated, memory 306 includes a non-volatile portion 310 and a volatile portion 312. Non-volatile portion 310 of memory 306 represents memory for maintaining persistent applications and/or data. Volatile portion 312 of memory 306 represents storage for maintaining non-persistent applications and/or data. According to particular design considerations, the medical information management application and practice, location, and user configuration data may be stored in the non-volatile portion 310 of memory 306, while medical professional, location, practice activity, patient data, and case information retrieved from a medical information management system may be stored in the volatile portion 312 of memory 306. Such an implementation provides added security to critical data and helps to ensure that confidential user, patient, and/or case information is not readily accessible even if mobile device 300 is lost or otherwise compromised. In some implementations, some or all of the practice, location, and user credentials may be stored in non-volatile memory to facilitate seamless access and/or quick reentry into the system, while some other credential may be stored in volatile memory to ensure that a lost device cannot be improperly used.

Mobile device 300 also includes a user interface 308. User interface 308 represents any appropriate combination of hardware, control logic, and data for displaying information to a user and receiving inputs from a user. Thus, user interface 308 includes any input and/or output interface. For example, a user interface may be a touch screen interface that is capable of both displaying graphical information and receiving user inputs. User interface 308 of mobile device 300 may be used to display medical case information using a medical information management application, and receive real-time updates of medical case information for appropriate processing and forwarding by the medical information management application.

In particular embodiments, mobile device 300 is capable of transmitting, receiving, and modifying medical case information to track changes occurring in real-time at a medical facility and forward such information to a medical information management system. Mobile device 300 may be used by medical professionals to receive real-time information corresponding to one or more cases and enter real-time updates for transmission to a medical information management system. Such updates, in turn, can be delivered to other computing devices or systems. In particular embodiments, mobile device 300 must transmit updates to medical information management system 120, which controls whether data is actually updated. Thus, a handheld device, such as mobile device 300, enables medical case information to be managed and coordinated between medical professionals actively rendering care to one or more patients.

In operation, elements of mobile device 300 perform various functions including facilitating maintenance and display of a graphical case board, enabling entry and display of medical professional activity information and patient treatment records having case chronology information, facilitating case status alerting for tracked medical cases, providing an intuitive graphical user interface for interacting with the system, enabling tracking of medical case assignments and roles in addition to handing-off assignments and roles between medical professionals, and facilitating secure authentication and access techniques.

To provide a graphical case board, mobile device 300 retrieves and presents information maintained by medical information management system 120. For example, processor 304 may execute a medical information management application residing in a nonvolatile portion 310 of memory 306 to receive medical case board information. Once this information is received, mobile device 300 may display a graphical case board using user interface 308. In operation, user interface 308 may graphically present multiple predefined phases of care in multiple tabs where each tab is selected through the user interface 308. In particular embodiments, each tab may correspond to a single predefined phase of care. In those embodiments, user interface 308 may receive user selections for each tab to display patient entries for patients for the corresponding predefined phase of care. In an embodiment designed for an anesthesia practice, the predefined phases of care may correspond to schedule, pre-operation, intra-operation, and post-operation stages for providing anesthesia care.

In some embodiments, each tab corresponding to a predefined phase of care may present a list of rows of patient tracking entries that list pertinent case information from a patient tracking record. This may include, for example, a patient information such as the patient's name, the medical procedure, the attending physician, surgeon, or anesthesiologist, any supervising or assisting medical professional, the operating room, scheduled operating room time, case role information, and any specific sub-events within the predefined phase of care such as the last anesthetic or surgical event with the corresponding time.

In operation, as a patient proceeds through medical phases of care, patient tracking entries may transition from being listed under the tab for one predefined phase of care to another. For example, in an anesthesia practice, the event of a patient arriving at a medical facility may cause a patient tracking entry to transition from being listed under a "schedule" phase to a "pre-operation" phase. Similarly, when an update indicating anesthesia administration is started for a patient, the corresponding patient tracking entry may transition from a "pre-operation stage" to an "intra-operation phase." When an update indicating that anesthesia administration has ended, the patient tracking entry may transition from a "intra-operation" phase a "post-operation" phase. At some predetermined point in time, such as midnight, all post-operation cases may be clear (with potentially exceptions for cases completed within a set period of time near midnight). Thus, the functionality provided by a graphical case board interface can receive updates to track real-time transitions between phases of medical care at a defined medical practice location.

In addition, selecting a row corresponding to a patient may cause the medical information management application to retrieve either a patient treatment record or case summary information. In one implementation, if the medical professional has a role associated with the case, a patient treatment record may be presented. If the medical professional does not have a role associated with the case, then case summary information may be presented. Mobile device 300 can request a patient treatment record or case summary information using network interface 302 to communicate across the communication network to the medical information management system. Mobile device 300 can also receive corresponding patient treatment record or case summary information for display on user interface 308 using network interface 302.

In addition to displaying the predefined phases of care for all cases corresponding to a medical practice at a defined location, mobile device 300 is capable of tracking medical events corresponding to a specific patient. In some embodiments, mobile device 300 may graphically display either a patient treatment record or a case summary based on whether the medical professional using this system has a role associated with the case. A patient treatment record corresponds to a single case and may include a case chronology that specifies timing of events during treatment. For the purposes of tracking timing and other related information, a patient treatment record may include a time record for medical events in the case chronology of the patient treatment record. A case summary may include case details for a specific case and facilitate the assumption or handing-off of medical roles with respect to the case.

Mobile device 300 is capable of presenting a patient treatment record in a graphical form on user interface 308. In some implementations, a patient treatment records may be presented in a tabbed interface. For example, a patient treatment record may be organized and displayed under multiple selectable tabs. One tab may present information corresponding to the case in a summary form including patient and medical procedure information. Another tab may list a chronology of related medical events for a medical procedure corresponding to the selected case based a predefined template for the medical practice. For example, listed medical events for an anesthesia practice may include, preparation start and stop, anesthesia start and stop, antibiotic administration, intubation, and surgery start and end. Each medical event that is presented in the chronology tab may be selected to log a timestamp corresponding to the medical event in a corresponding time record. Among other things, the time record for each presented medical event may have a current value of time, which could be a specific time value or no time value at all, for example, in the case of previously unrecorded medical events. Logging timestamps as the new current value for a time record permits the proper recording of the time for a billing-related event. For example, the beginning of anesthesia may be logged by selecting anesthesia start and the end of administering anesthesia may be logged by selecting anesthesia stop. In particular embodiments, selecting a billing-related event presents an interface for allowing the user to accept the current time as the time value for a timestamp. Determining a difference between two such timestamps facilitate the generation of appropriate invoices and reports for billing-related events. As changes or updates to a patient treatment record occur, corresponding changes and updates to case board information may also be triggered. Thus, other users can view a graphical representation of case board information, which includes information corresponding to the updated patient treatment record.

The graphical representation of a patient treatment record may also include a tab for checklist items for recording medical events that occur during a medical procedure but may not have a time or duration associated with them. Such events may include having to insert an extra intravenous line for a patient or other events that are performed for a medical procedure on an as needed basis. In addition, the checklist items may be displayed under appropriate categories or subcategories. The order, content, number, and organization of checklist items may be defined based on a template maintained for the practice or location at a medical information management system. Also, the tab for checklist items may be pre-populated based on rules triggered by non-checklist data or other checklist items. In operation, selecting a specific checklist item may cause the toggling of a YES/NO indicator for specifying whether the item has occurred during the case. Thus, the checklist presentation may entail a summary view that facilitates checklist data review, and a checklist entry view that facilitates toggling a state (e.g. YES/NO) for a particular checklist item. In some implementations, checklist items can be used to ensure quality control by requiring medical professionals to indicate whether specific policies or steps were followed. In addition to case specific items presented in a tabbed form, the graphical patient treatment interface may also include a contextual return tab for returning to the graphical case board. For example, the graphical patient treatment interface may have a back tab labeled according to the previous screen (e.g. "Board" for the graphical case board), which if selected, causes the graphical case board to be displayed on user interface 308.

Mobile device 300 is also capable of displaying a case summary interface for presenting a list of relevant medical information corresponding to a case. In certain implementations, when the user selects a particular patient tracking entry in the graphical case board interface but has no role associated with the case, the medical information management application of mobile device 300 causes the user interface 308 to display the case summary interface. The presented case summary information may include a patient identifier, the specific medical procedure, the attending surgeon, any anesthesiologists that are supervising or managing the case, any procedure or diagnosis codes, specific case identifiers and any other detailed information about the selected case or patient. In addition, the information presented may include relevant medical events of the case that have occurred or are currently taking place. In some implementations, this allows medical professionals to view case details for cases for which they do not have a role but may wish to now assume a role. In those implementations, medical professionals can assess a case in summary form prior to assuming a role. Some embodiments may also include color and/or icon depictions of data incompleteness. The manner in which data incompleteness is indicated is configurable based on location-specific rules and/or templates. Thus, the case summary interface presents a variety of relevant information to the user in an accessible form.

Some embodiments of the graphical case summary interface may also include multiple tabs. The tabs may correspond to specific roles that a medical professional can assume with respect to the case. For example, these roles may include assisting, supervising or directing, and personally providing care on the case. For an anesthesia practice, these roles may correspond to responsibilities associated with the administration of anesthesia. User interface 308 may receive a selection corresponding to a role, and in response, may require confirmation. If confirmed, mobile device 300 may then transmit a role-handoff request to medical information management system 120. If the information management system authorizes the role-handoff, mobile device 300 may receive a confirmation that the role assumption has occurred and, in response, present a case summary which includes the new assumed role. In particular implements, the graphical case summary interface may also include a contextual return tab for returning to a graphical case board interface. For example, a contextual return tab labeled as "Board" may be selected using the user interface 308 for returning to a graphical case board interface.

Embodiments of mobile device 300 may also provide case alerting functionality for necessary medical professionals. As discussed, case alerts may be automatically generated or be initiated by a user. Case alerts may take on a variety of forms including voice, text, or multimedia. For example, a user of mobile device 300 may be notified when a case that is being managed by the user of mobile device 300 enters a particular predefined phase of care. As an additional example, another case alert may cause a party being relieved to be notified when a role-handoff is successfully processed. In operation, mobile device 300 is capable of receiving a case alert corresponding to a case on network interface 302 for processing by a medical information management application being executed by a processor 304. After appropriate processing of the case alert, mobile device 300 may present the case alert on user interface 308 in any appropriate form. For example, mobile device 300 may present the case alert as a pop-up that may require the user of mobile device 300 to acknowledge receipt of the case alert or even take some action, such as accept a role-handoff request. In other embodiments, the case alert may be presented in a non-intrusive form such as a sliding banner or a pop-up that fades away after a predefined time interval. In this manner, the user of mobile device 300 is informed of relevant case events corresponding to a patient undergoing a medical procedure at a defined location. In certain embodiments, mobile device 300 may facilitate responding to case alert messages, for example, to acknowledge the receipt of the alert or to otherwise engage other medical professionals to take appropriate action in response to the indicated case event. In those embodiments, the response may be received by user interface 308 and the medical information management application being executed by processor 304 may process the response for delivery to a remote medical information management system over a communication network using network interface 302. The medical information management system may then process the response and forward corresponding messages to one or more handheld devices and/or systems as appropriate.

Users of mobile device 300 may also manually initiate their own messages for delivery to other systems to request information related to a case or provide information about a case to appropriate medical professionals. In certain embodiments, user interface 308 may present a predefined list of user initiated messages for delivery to other medical professionals corresponding to a medical practice. For example, messages included in a predefined list includes but are not limited to "need break," "need assistance," "induction," "emergency," or other suitable predefined message. In alternative embodiments, user interface 308 may facilitate the entry of user initiated messages in a free form field. In those embodiments, user interface 308 may facilitate the entry of fully customizable messages for addressing concerns with respect to a case, or any real-time need associated with a medical practice or procedure. Accordingly, mobile device 300 supports automatic and user-initiated case alerts for coordinating and interacting with medical professionals associated with a medical practice.

While mobile device 300 is illustrated as including specific components, it should be understood that various embodiments may operate using any suitable arrangement and collection of components.

Figure 4:
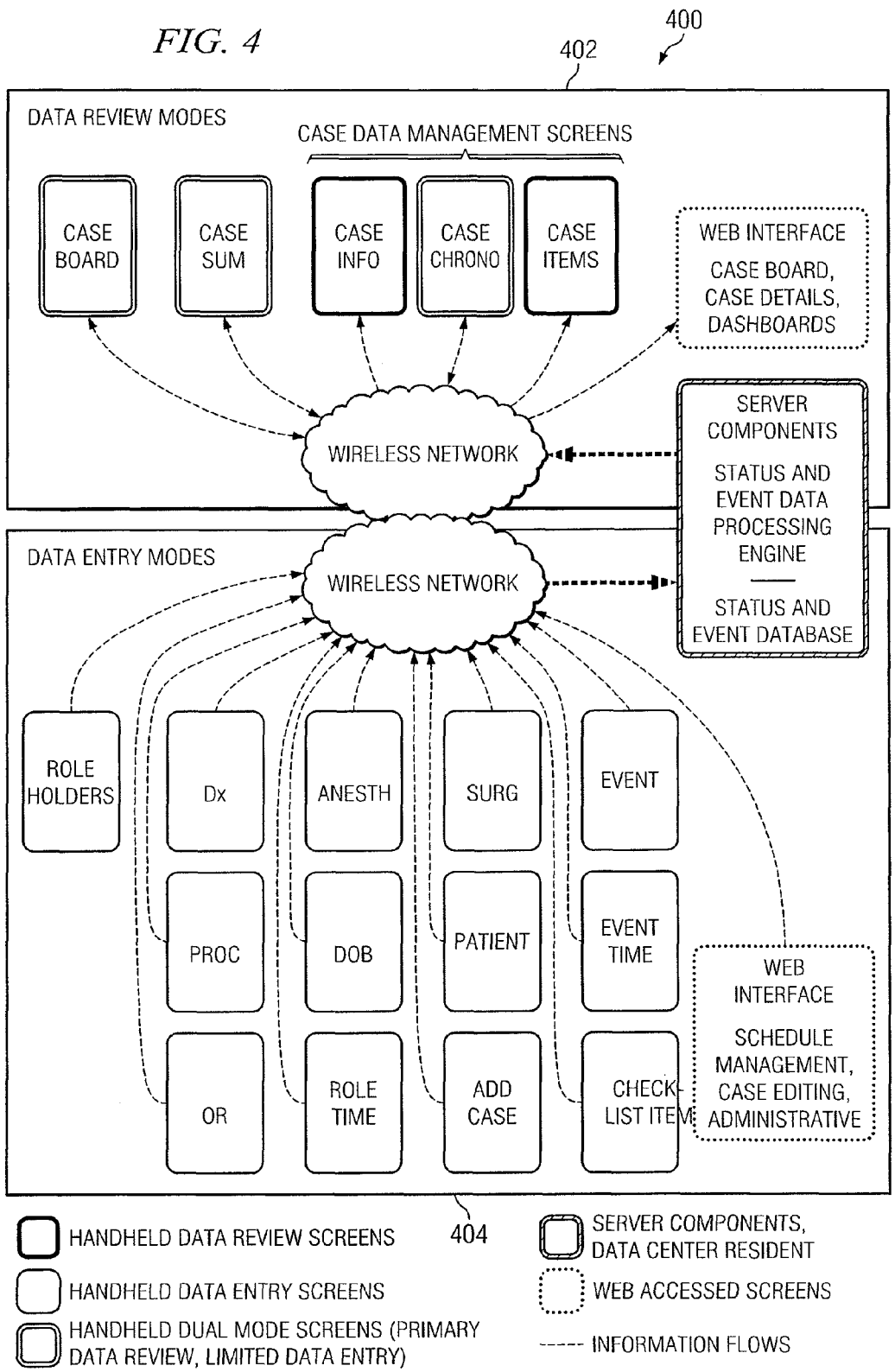
FIG. 4 is a system architecture diagram describing an example user interface for a medical information management application operating on a handheld device.

FIG. 4 is a diagram illustrating a system architecture 400 for describing a user interface for a medical information management application operating on a handheld device. As illustrated, system architecture 400 includes a collection of data review modes 402 and a collection of data entry modes 404. In general, the data review modes correspond to display modes of the graphical user interface that facilitate the display of medical case board information, patient treatment information, and case summary information. The various data review modes 402, permit users of the system to review real-time data for multiple concurrent cases. Data entry modes 402 represent a collection of display modes for entering case-specific information. Data entry mode 404 enable multiple users of the medical information management system to enter data for multiple concurrent cases of a medical practice. Thus, the various display modes of system architecture 400 together provide an intuitive graphical interface for data entry and retrieval for cases associated with a medical practice.

Figure 5:
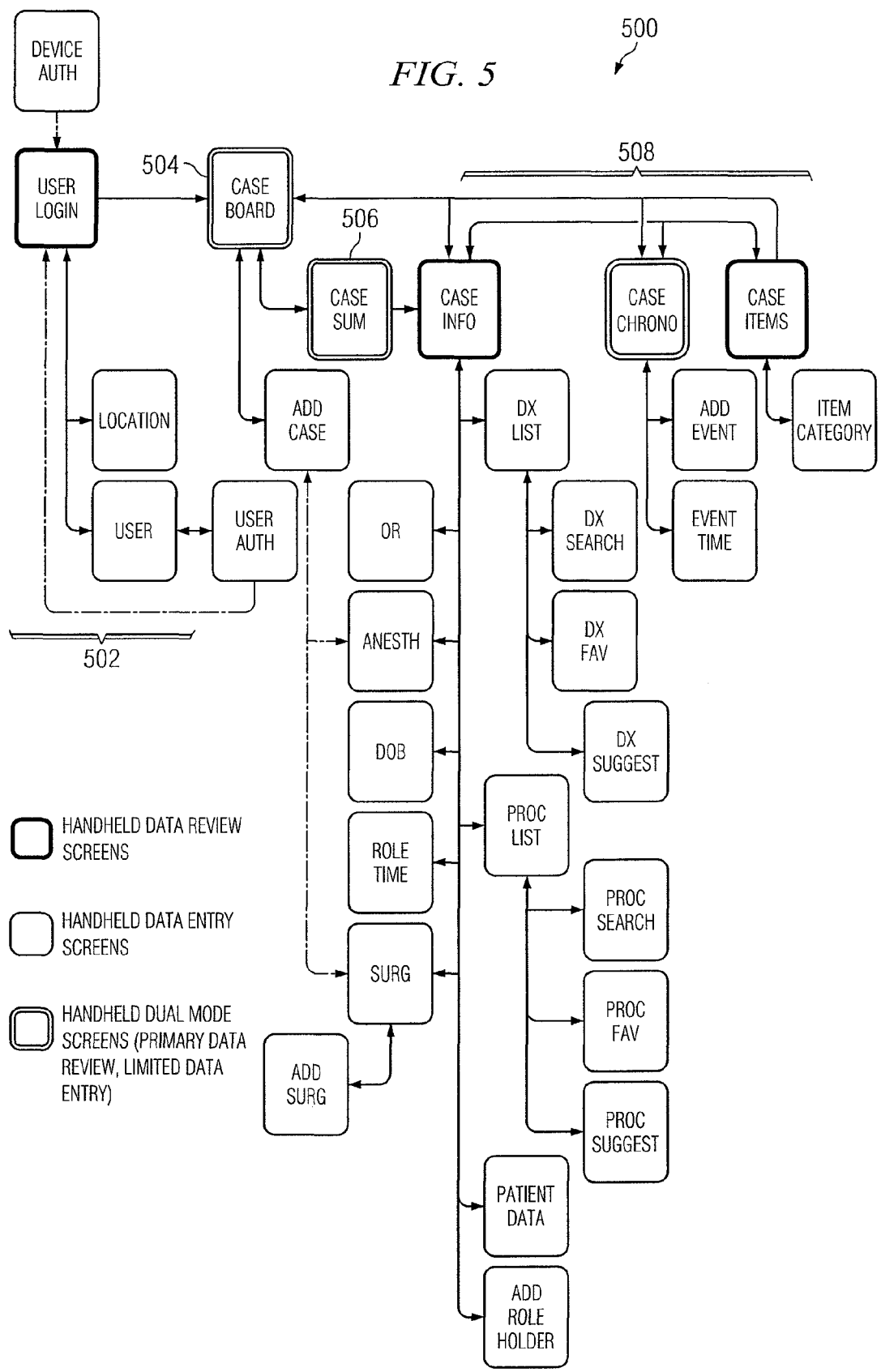
FIG. 5 illustrates an example system hierarchy of a graphical user interface on a handheld device.

FIG. 5 is a system hierarchy 500 for a graphical user interface on a handheld device. As illustrated, system hierarchy 500 includes a number of modes corresponding to display modes of a graphical user interface, including a user login interface 502, a case board interface 504, a case summary interface 506, and a patient treatment interface 508. As illustrated, these display modes may be used to display case information and facilitate data entry for cases in an efficient manner using the graphical user interface at a handheld device, such as mobile device 300.

System hierarchy 500 shows a first display mode having a user login interface that first requires a device authentication. In operation, device authentication may be performed by comparing a practice or user key code (or any other suitable identifier) to values stored in a medical information management system. Once the device itself is authenticated, the graphical user interface may provide an interface for indicating a medical practice and selecting an authorized user corresponding to the medical practice. Once a user is selected, the device may receive a password and PIN from the user. Once the user is properly authenticated with the medical information management system, the graphical user interface may display a list of one or more supported locations for a medical practice. In some implementations, these locations correspond to medical facilities for providing care to patients. In operation, the selection of a location may cause the display of case board interface 504. The case board 504 provides information regarding all cases at a defined location organized into predefined phases of case. The case board interface is further operable to receive a selection of a case corresponding to a particular patient. In response to receiving a selection, a case summary interface 506 or patient treatment interface 508 may be displayed based on design considerations. The case summary interface 506 provides detailed information about a particular case, including both patient-specific information and current information regarding medical events corresponding to an ongoing or scheduled medical procedure. In particular implementations, a case summary interface is presented when a user is not affiliated with the case. A user may not be affiliated with a case, for example, when the user has not assumed an active role with respect to the case.

In other implementations, selecting a particular case at the case board interface 504 causes the graphical user interface to proceed to a patient treatment interface 508. According to design considerations, patient treatment interface 508 may be presented if the user using the graphical user interface actually has an active role in the selected case. For example, as shown in the illustration, a patient treatment interface 508 may present a patient treatment record in three different display modes. One mode may present patient and case information in such a manner that facilitates modification of specific data elements. Another display mode may display case chronology and facilitate the tracking of medical events for the case in corresponding time records. Another display mode of patient treatment interface 508 may permit the recording of case data items corresponding to medical events or items not having a time or duration associated with them. Such case items may be listed in a checklist form. In some embodiments, checklist items may include case items for ensuring quality control or conformity with institutional policies for a medical practice. Thus, the hierarchy of display modes of system hierarchy 500 facilitate streamlined access to medical case information in an aggregate form through case board interface 504, and the real-time tracking of specific cases through patient treatment interface 508.

Figure 6:
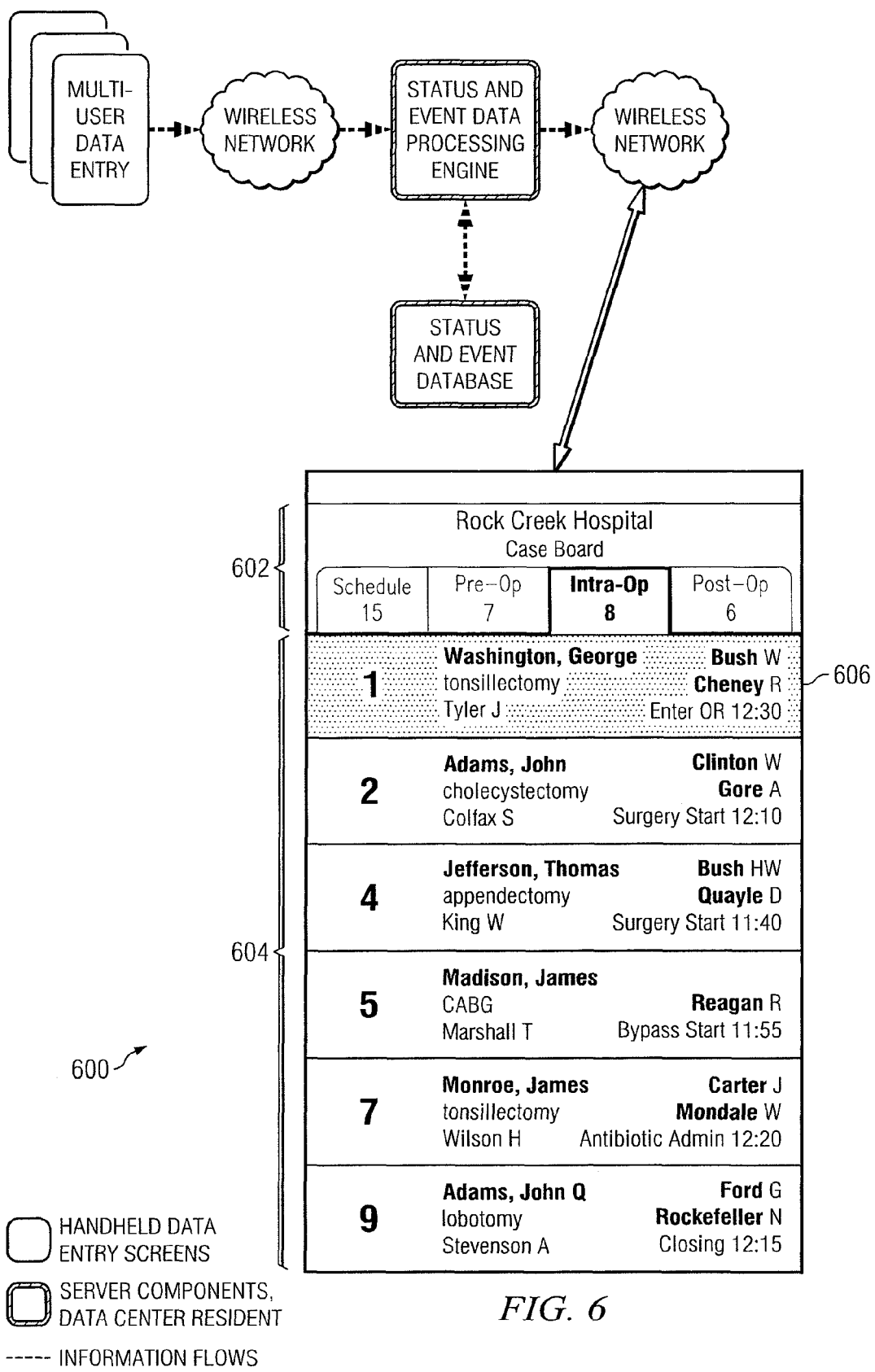
FIG. 6 illustrates an example case board interface presented on a handheld device for interacting with a medical information management system.

FIG. 6 is a diagram illustrating a case board 600 representing an example graphical case board interface for a handheld device interacting with a system according to the present disclosure. As shown, case board 600 includes various elements that together provide a distinctive interface for interacting with the graphical case board. In the illustrated embodiment, case board 600 includes two elements: case board tabs 602 and multiple patient tracking entries 604. Among the patient tracking entries 604 is a user-affiliated patient tracking entry 606. The displayed user interface, organization of patient entries and phases of care, color and other visual schemes, level of detail, and other information displayed by case board 600 may be customized based on the particular user, practice group associated with the user, location at which the user is working, or other appropriate settings and data. In addition, some embodiments may also include color and/or icon depiction of data incompleteness. The manner in which data incompleteness is indicated is also configurable based on location-specific rules and/or templates.

As illustrated, case board tabs 602 of case board 600 represent an organization of patient tracking entries according to predefined phases of care corresponding to a medical practice at a defined location. These predefined phases of care may be defined in a template configured for a medical practice and maintained by a central medical information management system. In the illustrated embodiment, each of the case board tabs 602 correspond to a phase of providing anesthesia care. For example, the "schedule" phase corresponds to a phase of providing medical care where each of the patients listed are scheduled but have not yet arrived in the peri-operative area. Another phase, an anesthesia pre-operation phase shown in the illustration as "pre-op," represents a phase of care prior to an anesthetic (or surgical) procedure where patients are waiting in the surgical holding room or pre-operation area. The next tab corresponds to an intra-operation phase shown in the illustrated embodiment as "intra-op." The intra-operation phase represents a phase of care wherein the patients have in-process anesthetics or are in the operating room. Finally, the last tab corresponds to a post-operation anesthesia phase, shown in the figure as "post-op." This final stage corresponds to a phase of care after the anesthetic (or surgical) procedure where the patients are in the surgical recovery room or post-operation area.

In operation, each of the illustrated tabs may be selected to list patient tracking entries corresponding to that phase. For example, in the illustrated embodiment, "intra-op" is currently selected and corresponding patient tracking entries 604 are displayed. Case board tabs 602 may also indicate case count information as shown by the numbers below each labeled tab for a predefined phase of care. These numbers allow a user presented with case board 600 to determine, at a quick glance, how many patient tracking entries can be found under each of the case board tabs 602. In certain implementations, the case count may correspond to the number of cases under each of the case board tabs 602 that correspond to the user. For example, the case count may be the total number of cases within a predefined phase of care for which the user has a case role. Thus, the case board tabs 602 provide a user-friendly organization of patients as they proceed through predefined phases of anesthesia care.

As specific patients associated with the patient tracking entries progress from one predefined stage to another, case board 600 may be updated with appropriate listings under the corresponding case board tabs 602, potentially in real-time as these changes occur in the field. For example, when a user of a particular mobile device 118 provides a patient treatment update indicating that a patient has begun receiving anesthesia, and medical information management system 120 transitions that patient from a pre-operation stage to an intra-operation stage, and all mobile devices 118 tracking that patient or that patient's surgical location can be updated. Accordingly, the corresponding patient tracking entry transitions from being listed under the illustrated "pre-op" tab to being listed under the illustrated "intra-op" tab. The case count information corresponding to the tabs may also be updated to reflect such transitions.

The illustrated embodiment of case board 600 shows multiple patient tracking entries 604. Each patient tracking entry of patient tracking entries 604 corresponds to a particular predefined phase of care indicated by the appropriate case board tab. As illustrated, multiple patient tracking entries 604 are listed for the intra-operation phase of anesthesia care. In particular, each patient tracking entry has specific information corresponding to the indicated case. For example, as the illustration shows, the patient tracking entry may include patient information such as the patient's name, the medical procedure, the assigned operating room, the attending surgeon/physician, the anesthesiologist and any supervising anesthesiologist, and sub-events within the predefined phase of care such as surgery start, entering an operating room, or an antibiotic being administered. In addition, each of these sub-events may include a timestamp indicating when the sub-event occurred. In particular embodiments, case board 600 may display icon-based depictions of specific medical events or status for a given case.

The illustration also shows a user-affiliated patient tracking entry 606 of patient tracking entries 604. In particular embodiments, case board 600 may cause the list of patient tracking entries 604 to be sorted where cases affiliated with the user are brought to the top of the list. For example, user-affiliated patient tracking entry 606 is shown at the top of the list of patient tracking entry 604 because it is affiliated with the user of the handheld device on which case board 600 is being displayed. A user affiliation, for example, may be established when the user of case board 600 has a particular role with respect to the indicated case. Also, as shown in the illustration, user-affiliated patient tracking entry 606 may be highlighted using color or some other suitable visual emphasis. In addition to distinguishing the user-affiliated patient tracking entry 606 from other patient tracking entries, the provided visual emphasis may further indicate the nature of the role that the user of case board 600 has with respect to the patient indicated by the patient tracking entry. For example, case board 600 may use a color scheme defined for the practice where one color indicates that the user is in a supervisory role and another color indicates that the user is actively providing care for a case identified by the patient tracking entry. While a color scheme is disclosed by this particular illustration, any suitable visual emphasis for separating user-affiliated patient tracking entries from other patient tracking entries is envisioned by the present disclosure. The information displayed in the rows corresponding to user-affiliated patient tracking entries, such as user-affiliated patient tracking entry 606, may be further based on the user's case role. For example, a user-affiliated patient tracking entry where the user is in a supervisory role may result in particular information being displayed in a particular format. Another user-affiliated patient tracking entry where the user is actively providing care, for example, may result in other information being displayed and/or another information format being used. The illustrated embodiment also indicates that case board 600 relies on receiving case status and event data from a remote medical information management system which is updated in real-time by multiple medical professionals actively engaged in patient care at a practice location.

In operation, each of the patient tracking entries 604, including user-affiliated patient tracking entry 606 are capable of being selected through a user interface. The selection of one of the patient tracking entries 604 may result in either a case summary or patient treatment interface being displayed. Design considerations may dictate which one of these interfaces is displayed. For example, in the illustrated embodiment, selecting user-affiliated patient tracking entry 606 may result in the patient treatment interface being displayed since the user of case board 600 has a specific role with respect to the user-affiliated patient tracking entry 606. If one of the other patient tracking entries are selected, a case summary interface is displayed. A case summary interface lists details about a particular case including relevant medical events and specific medical data corresponding to the patient (e.g. patient identification and medical history). In certain implementations, the case board 600 may be visually distinguished from a patient treatment and/or case summary interface. For example, the case board may be monochromatic while the patient treatment interface and/or case summary interface may use colorful tabs or menu selections. Case board 600 may also be operable to receive a user request for a refresh of the case board information. For example, shaking the device may generate a case board refresh request that causes case board 600 to fetch updated case board information from a remote medical information management system for display on the graphical case board interface. Thus, case board 600 provides a user-friendly interface for tracking all medical cases for a medical practice at a particular location.

Figure 7:
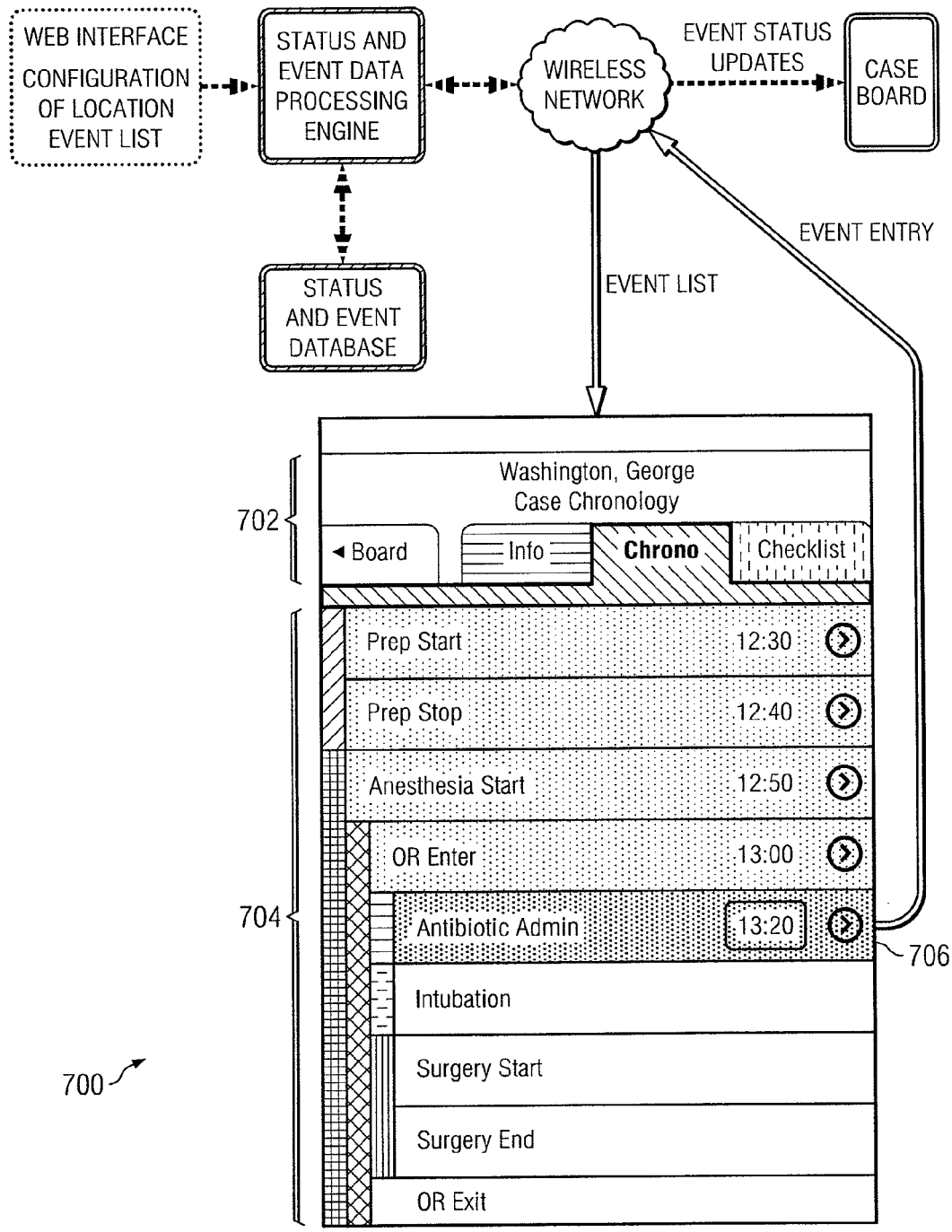
FIG. 7 illustrates an example patient treatment interface for displaying patient treatment information for a specific medical case.

FIG. 7 is a diagram illustrating an example patient treatment interface 700 for displaying a patient treatment record for an active case at a medical practice. As described, the patient treatment interface 700 may be displayed when a graphical user interface of a handheld device presenting a case board 600 receives a user selection corresponding to a specific patient tracking entry. The displayed user interface, organization of case and checklist items, specific medical events, color, icons and other visual schemes, the level of information detail, and other information displayed by patient treatment interface 700 may be defined by a template configured for a medical practice and maintained remotely by a medical information management system. For example, some embodiments may also include color and/or icon depiction of data incompleteness. The manner in which data incompleteness is indicated is configurable based on location-specific rules and/or templates. The illustrated embodiment shows patient treatment interface 700 as including patient treatment tabs 702 and case chronology events 704 corresponding to a chronology of medical events for a particular case at a medical facility. Unlike checklist items, these medical events typically have or will have a time value or duration associated with them. Among the case chronology events 704, is an antibiotic administration event 706 shown as the last recorded medical event.

Patient treatment tab 702 of patient treatment interface 700 provides a tabbed interface for displaying case specific information. In the illustrated embodiment, patient treatment tab 702 includes four tabs. While the first tab facilitates return to the graphical case board 600, the other tabs provide further details for the selected case. For example, the information tab provides detailed information about the patient, such as medical history and other identifying data along with relevant medical events corresponding to the medical care being provided. Another tab, shown as the checklist tab, lists specific case items in a checklist format. These items correspond to medical events that may be necessary on an as needed basis during a medical procedure but do not have a time or duration associated with them. Thus, for example, an anesthesiologist may record a medical event that became necessary for a particular patient, such as starting an extra intravenous line, which may not include a time value or duration. Other case items may relate to quality control measures or institutional policies enforced by a medical practice. Finally, the selected chronology tab displays medical events for a particular medical procedure shown in the illustrated embodiment as case chronology events 704. As shown, the case chronology events have timing associated with them, which may be recording in an appropriate time record. Further, patient treatment tabs 702 may be visually distinguished from each other to discern one tabbed display mode from another.

In the illustration, the chronology tab of patient treatment tabs 702 is selected. The chronology tab displays multiple case chronology events 704. Each of these case chronology events corresponds to an medical event for the medical procedure corresponding to the selected patient and may have an associated time record for recording a time value or duration. The medical events that are listed under the chronology tab may be defined by a practice and/or location-specific template maintained by a medical information management system. For example, as the illustration shows, these events may include prep start, prep stop, anesthesia start, operating room (OR) enter, antibiotic admin, intubation, surgery start, surgery end, and OR exit. Other events may include, arrival in the holding room, anesthesia stop, bypass start/stop, heart stop/start, C-section start/stop, vaginal delivery start/stop. Case chronology events 704 may be visually nested to define relationships between collections of events. For example, all case chronology events between OR enter and OR exit are considered part of an operating room event. This relationship is shown by the indentation of associated sub-events relative to the case chronology events that they are considered to be part of. For example, antibiotic admin, intubation, surgery start and surgery end rows are indented in relation to OR enter and OR exit to show that those events are to take place between entry and exit of the operating room. Patient treatment interface 700 also illustrates nested relationships and the relative duration of medical events by visually emphasizing the range of medical events using color-coded vertical bars in the left margin. The colors or other visual emphasis for the vertical bars may be configured in a practice template maintained by a medical information management system. In certain implementations, some of the case chronology events 704 may facilitate visual reordering of medical events based on location or practice rules. At the same time, certain case chronology events 704 may not facilitate visual reordering if the location or practice rules prohibit it.

In operation, the rows corresponding to each of the case chronology events 704 are operable to receive a user selection through a user interface to cause the patient treatment interface 700 to record a timestamp corresponding to the appropriate case chronology event. This timestamp may be recorded in a time record corresponding to the event. For example, when a row corresponding to one of the case chronology events 704 is selected, patient treatment interface 700 may present a button enabling rapid entry of the current time as the timestamp for the selected case chronology event or present another interface, which allows the user to enter another time for the selected case chronology event. As shown, the last recorded event in the illustrated embodiment is "antibiotic admin" at time 13:20, which was recorded by selecting the arrow shown in the right margin of the row corresponding to antibiotic administration event 706. This time value may be recorded as the current value for the time record corresponding to antibiotic administration event 706. Other events such as intubation, surgery start and surgery end, and OR exit may be recorded in a similar fashion as the medical procedure progresses. Since these other events are unrecorded, their corresponding time records would have no current value at all. In operation, the patient treatment interface 700 is operable through the chronology tab to respond to the receipt of a user selection of one of the case chronology events 704, such as, for example, the antibiotic administration event 706, record a timestamp in the appropriate timing record and send an event update corresponding to the selected medical event over a network to central medical information management system. In this manner, other computing devices and systems managing case information can receive and review changes to case chronology events of a patient tracking record in real-time, including update of the last case event parameter on case board 600. In some implementations, patient treatment interface 700 may permit a medical professional to add new medical events using the graphical user interface. For example, selecting a specialty row for adding events may allow a user to define a new medical event for medical tracking purposes.

Some embodiments of patient treatment interface 700 may implement other features. For example, some of the case chronology events 704 may facilitate the reversal of a medical event recording. For example, selecting particular events may allow user to undo the recording of an event. This may be useful to correct user entry errors, or for other medical reasons. Based on design considerations, certain medical events may be irreversible as defined by the associated medical practice. For example, a particular medical practice may not choose to allow medical professionals rendering anesthesia care to undo the event of anesthesia start. Some embodiments may display a countdown timer for indicating the time remaining for a medical procedure, and this information may be transmitted in real-time to a medical information management system. As yet another feature, the patient treatment interface 700 may also be operable to receive a user request for a refresh of the patient treatment information. For example, shaking the device may generate a refresh request for a patient treatment record that causes patient treatment interface 700 to retrieve updated patient treatment information from a remote medical information management system for display on the graphical case board interface. Thus, patient treatment interface 700 provides an user-friendly interface for tracking and recording medical events in real-time.

Figure 8:
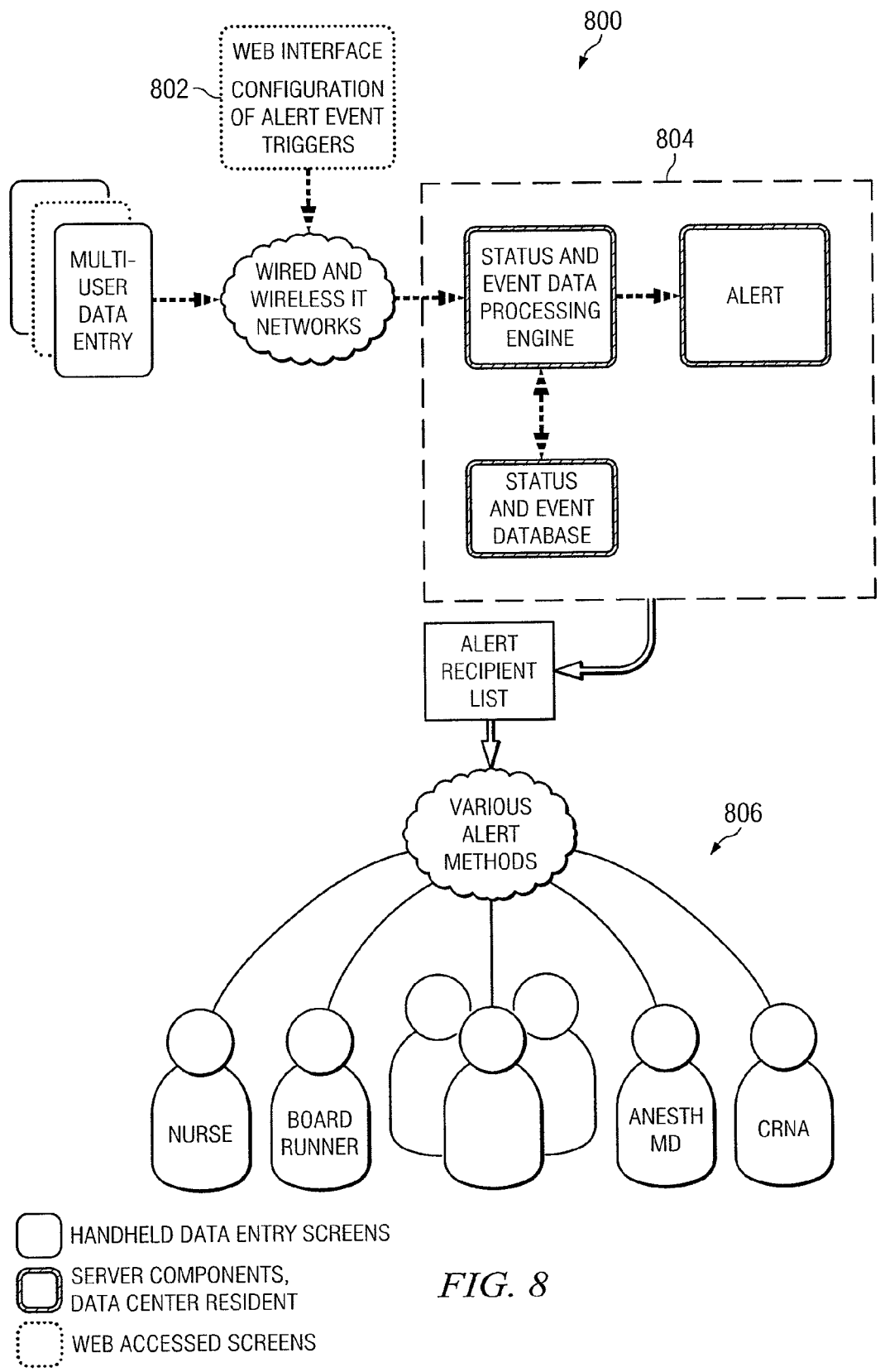
FIG. 8 is a block diagram illustrating an example case alert system for sending, processing, and transmitting case alerts to users of a medical information management system.

FIG. 8 is a block diagram illustrating a case alert system 800 with elements that interoperate to receive, process, and transmit case alerts to various users of a medical information management system. The elements of case alert system 800 can support a number of operations associated with generating and sending case alerts, including configuring alert event triggers for maintenance by a central case alert system processing, processing real-time medical events for comparison with alert event triggers to determine whether to issue a case alert, and formatting and transmitting case alert messages for delivery on various networks using disparate protocols. Various example networks for sending alerts include a wired/wireless computer network, pager networks, cellular SMS networks, email networks, and instant-messaging networks.

In the illustrated embodiment, case alert system 800 includes a number of elements that work together to alert one or more medical professionals. As shown, case alert system 800 includes an event trigger configuration interface 802, a case alert manager 804, and one or more intended recipients 806. Some or all of the functionality of system 800 may be provided by case alert module 204. As a particular example, the functionality of case manager 804 may be implemented in case alert module 204 of system 200.

Event trigger configuration interface 802 represents any suitable interface for configuring medical events for which a case alert should be issued to one or more intended recipients 806. For example, an event trigger configuration interface 802 may be a web interface for supplying a case alert manager 804 with specific event triggers. In addition, the event trigger configuration interface 802 may couple to an appropriate communication network to transmit event trigger configurations to case alert manager 804 for updating an appropriate database.

Case alert manager 804 represents appropriate hardware, control logic, and data for storing case alert configurations and determining when and how to issue an alert according to the configured event triggers. For example, case alert manager 804 may be a computer server or virtual computer server capable of processing case alerts. In certain implementations, case alert manager may be embodied in a module of a larger medical information management system, such as case alert module 204 of system 200.

Intended recipients 806 represent one or more medical professionals of a medical practice or surgical location indentified in an event trigger for receiving case alerts on the occurrence of predefined medical events. For example, as shown, the intended recipients may include a nurse, a case board runner, an anesthesiologist, or a CRNA. The actual alert method used to notify intended recipients 806 may conform to any appropriate protocol on any suitable network. For instance, a medical professional may receive case alerts in a text message using an SMS service or in an email using a wired/wireless network.

In operation, the case alert manager 804 may issue a case alert to one or more intended recipients 806 when a real-time medical event matches an event in a stored event trigger configured through an event trigger configuration interface 802. In particular, case alert manager 804 receives one or more event triggers through the event trigger configuration interface 802 for storage in an appropriate database. Next, case alert manager 804 monitors medical events for one or more cases in a medical practice. For example, case alert manager 804 may monitor updates to a central database maintaining case information tracking patients receiving care. Case alert manager 804 may then process these medical events to determine whether the identified medical events match the events in any stored event triggers. If a match is found, case alert manager 804 may issue a proper case alert message in an appropriate format and using a suitable network to notify one or more indicated intended recipients 806. Accordingly, embodiments of the present disclosure can receive, process, and send case alerts to facilitate coordination of medical activities for one or more cases.

Figure 9:
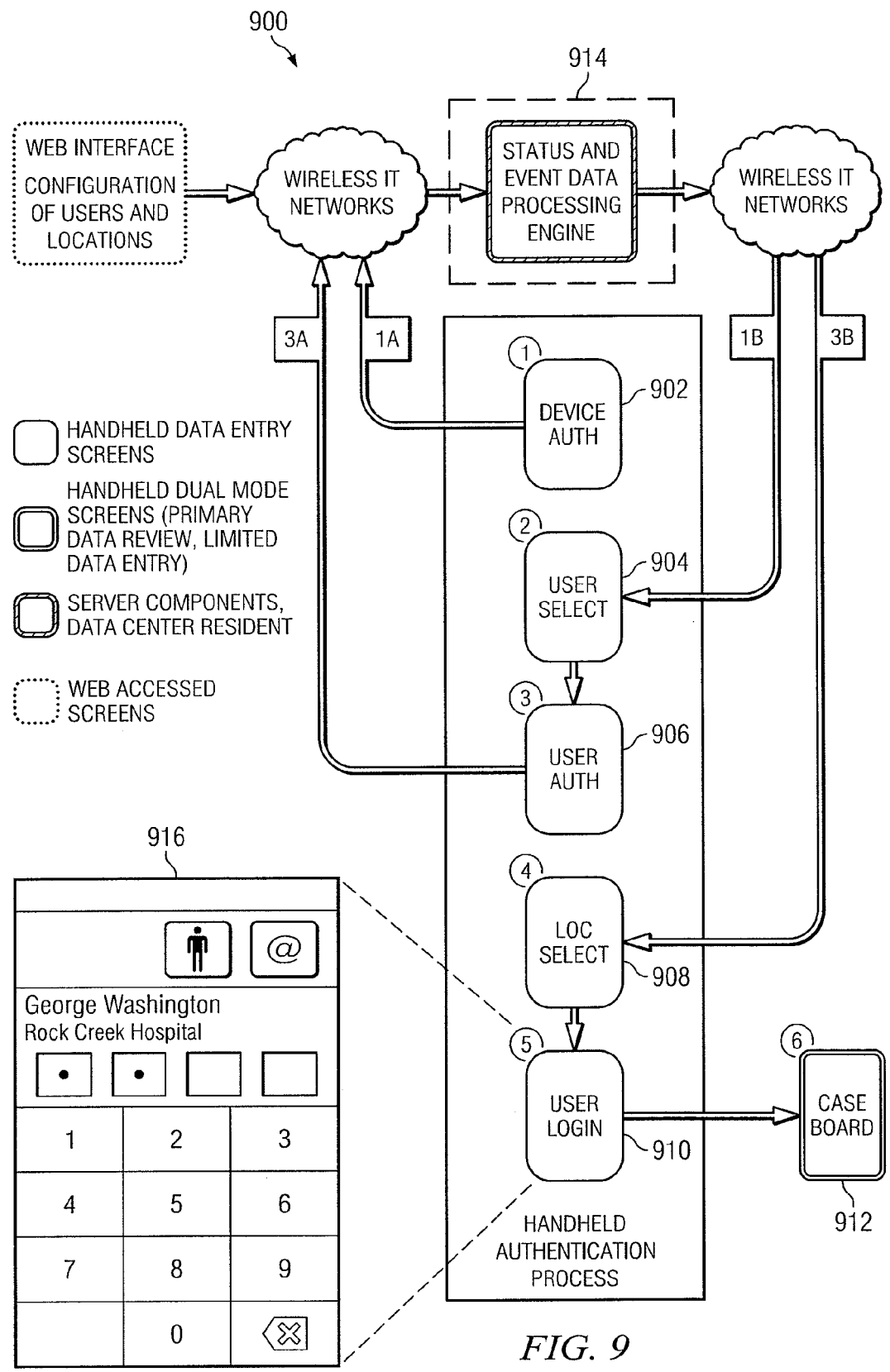
FIG. 9 illustrates an example process flow for secure authentication, login, and access to a medical information management system.

FIG. 9 is a process flow diagram illustrating a process flow 900 for secure user authentication, login, and access to a medical information management system. The steps of process flow 900 correspond to an example sequence of steps for securely accessing medical information from a medical information management system. Such an authentication process ensures that confidential patient information and medical case information are protected from unwanted disclosure. A user authentication process like process flow 900 may be implemented on the front-end of medical information management system such that access to features, functionality, and confidential information require users to be first authenticated by the system.

In the illustration, process flow 900 includes a number of steps for providing user authentication, login, and access to a medical information management system. As shown, these steps include a device authorization step 902, a user selection step 904, a user authorization step 906, a location selection step 908, a user login step 910 and a case board presentation step 912. This collections of steps may be performed, for example, on a handheld device, such as mobile device 300, through a graphical user interface interacting with a remote medical information management system.

The illustration also shows an authentication system 914 and an example user login interface 916. Authentication system 914 represents a system for authenticating and facilitating access users of the system. For example, authentication system 914 may be embodied in a larger medical information management system, such as system 200. The authentication system may be configured with users and locations through an appropriate configuration interface. For example, a web interface may be used to configure authentication system 914 with users and locations having access to the system. User login interface 916 represents an example user login interface for supplying a PIN to the authentication system 914.

In operation, process flow 900 begins at the device authorization step 902. In this step, the user of a handled device supplies a practice key identifying a particular medical practice or a user key identifying a user within a particular medical practice. This information is sent across a network via path 1A along with a device hash corresponding to the authentication system 914. The device hash ensures that only authorized devices may access the system, thereby providing a first level of access protection to the system. Once the practice key or user key and device hash are determined to be valid by authentication system 914, the system responds by sending two lists via path 1B over one or more networks to the handheld device: a list of authorized users for the identified medical practice and a list of specific practice locations for the medical practice.

Next, the graphical user interface of the handheld device proceeds to the user selection step 904. At this step the graphical user interface may be used to indicate one of the authorized users in the list supplied by authentication system 914. Process flow 900 then enters the user authentication step 906 where the graphical user interface may receive a password for the selected authorized user. Requiring the selection of an authorized user and corresponding password provides a second level of access protection to the system. User authentication step 906 may transmit this information over one or more networks to the authentication system 914 for validation, shown as path 3A of the illustration. Once the authentication system confirms that the password is valid, the authentication system sends a personal identification number (PIN) over a network through return path 3B to the handheld device. This PIN corresponds to the medical practice and the user identified from the authorized list of users delivered to the handheld device following device authorization step 902. Process flow 900 then proceeds to the location selection step 908 where a selection of a particular practice location associated with the medical practice is received by the graphical user interface. This causes process flow 900 to enter a user login step 910.

In operation, user login step 910 may present an appropriate user login interface such as, for example, the illustrated user login interface 916. The user login interface may accept a user-supplied PIN using the graphical user interface.

Requiring a user PIN specific to the selected authorized user provides a third level of access protection to the system. Once this information is received, user login step 910 may validate the user-supplied PIN against the PIN received from authentication system 914 following user authentication step 906. A validated PIN can be used again later after validation for quick access to medical information and functionality provided by the system, thereby obviating repeated validations of the practice key or user key and password corresponding to the selected authorized user. Finally, if the entered PIN is valid, process flow 900 proceeds to a case board presentation step 912.

In the illustrated embodiment, entering case board presentation step 912 indicates that all proper authentication steps for accessing the medical information management system have been properly processed and that access to the system has been granted. Thus, in the case board presentation step 912, the graphical user interface may display an appropriate interface for interacting with a medical information management system. Such an interface may include a graphical case board interface for performing various case-related functions corresponding to the selected medical practice and location. Some embodiments may support the retention of selected authorized user and location information for rapid system re-entry which may require a subset of the original authentication information as user input. Similarly, in some implementations where there are more than one locations associated with practice, entering another practice location may only require an appropriate subset of the original authentication information as user input. For example, a graphical user interface may request entry of a user PIN to regain access to information and functionality supplied by a previously accessed medical information management system, or to switch practice locations. Thus, process flow 900 describes an example sequence of steps for user authentication, login, and access to a medical information management system.

While process flow 900 is illustrated as including specific steps, it should be understood that various embodiments may implement a user authentication login and access scheme using any appropriate combination of steps for providing secure access to a medical information management system.

Figure 10:
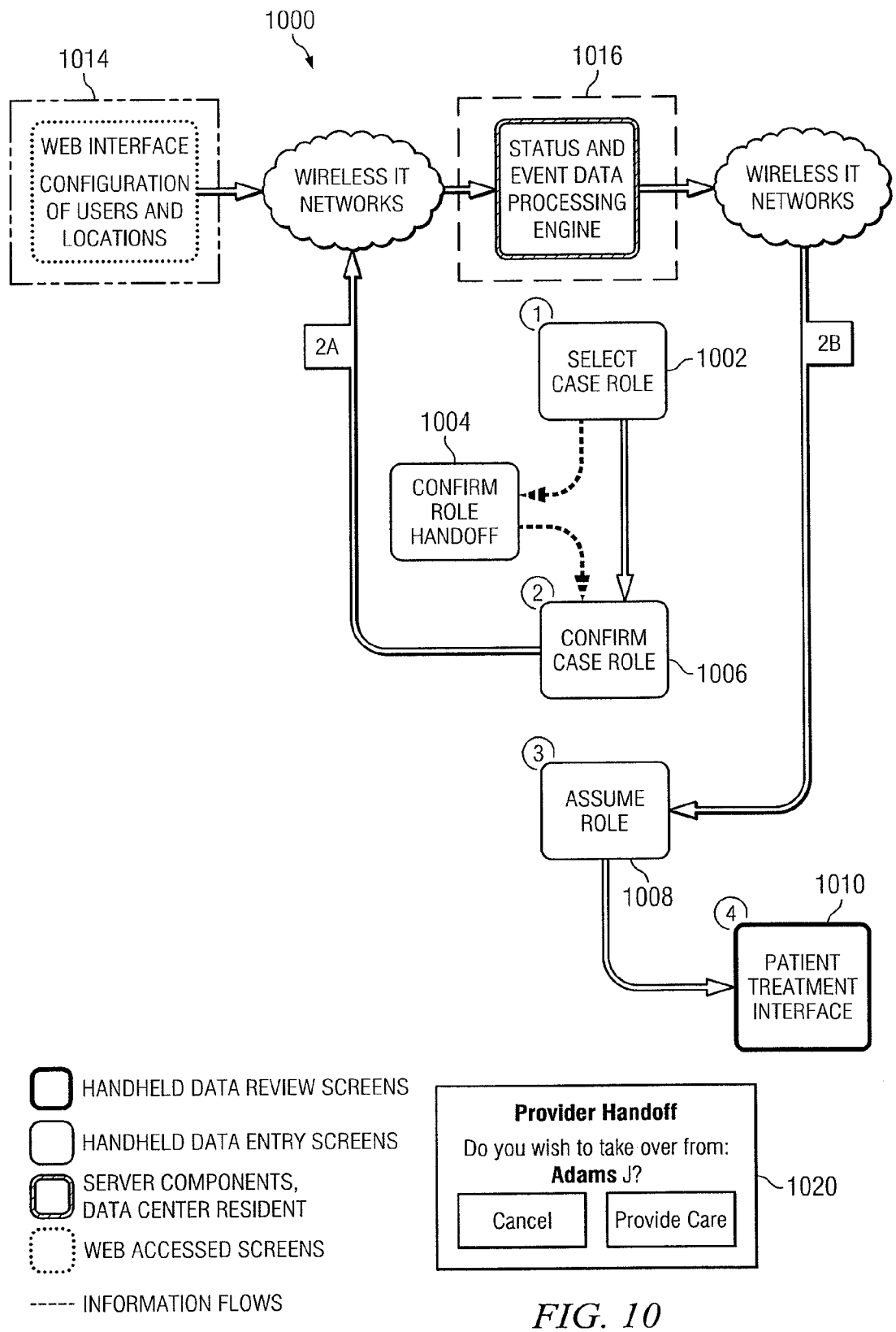
FIG. 10 illustrates an example process flow for conducting role-handoffs between users of a medical information management system.

FIG. 10 is a process flow diagram illustrating an example process flow 1000 for conducting role-handoffs between medical professionals associated with a medical practice or an anesthesia care location. As illustrated, process flow 1000 includes a case role selection step 1002, role-handoff confirmation step 1004, a case role confirmation step 1006, a role assumption step 1008, and a patient treatment interface step 1010. Various steps in process flow 1000 interact with other systems and interfaces. For example, the steps of process flow 1000 may interact with a user and location configuration interface 1014 and a case role management system 1016. An example role-handoff confirmation message 1020 for confirming a selected role-handoff is also illustrated.

Case role management system 1016 represents a system for managing cases and case role assignments at an anesthesia care location. For example, case role management system 1016 may be embodied as an element or combination of appropriate elements of a medical information management system, such as system 200. Thus, for example, case role management system 1016, may be implemented by business logic 210 of system 200. A user location configuration interface 1014 represents any appropriate interface for configuring assignments and case roles and communicating such configuration to a case role management system 1016. For example, a user location configuration interface may be web interface for configuring case roles over a network to case role management system 1016.

In operation, the illustrated process flow 1000 begins at the case role selection step 1002. As discussed, a role indicates a responsibility of medical professionals associated with a medical case. In case selection step 1002, a graphical user interface at a handheld device, such as system 300, permits a medical professional to select a case role. These case roles may be presented, for example, in a case summary interface describing a particular medical case. In certain embodiments, a tab of the case summary interface may receive a role selection for the case. For example, a user may select one of many tabs corresponding an assisting role, a supervisory or directing role, or a care provider role.

As shown in process flow 1000, once a case role is selected, case role selection step 1002 may proceed to an optional role-handoff confirmation step 1004. At this optional step, the graphical user interface may request confirmation of a role-handoff request when another medical professional currently has that role. This optional step thus confirms a medical professional's desire to relieve another medical professional who is already acting in that particular role with regard to a case. For example, a graphical user interface may present a role-handoff confirmation message 1020 to seek confirmation of a role-handoff from one specific medical professional to another. Thus, the option role-handoff confirmation step 1004 ensures that a role-handoff was not inadvertently requested.

In operation, the case role confirmation step 1006 is entered from the case role selection step 1002 or the optional role-handoff confirmation step 1004, as shown in the illustrated process flow 1000. In the case role confirmation step 1006, the graphical user interface seeks a confirmation from the user that a case role assumption is requested. For example, a graphical user interface may present a pop-up panel that appears momentarily on the screen for confirming a case role selection or handoff. Once confirmed, case role confirmation step 1006 communicates over one or more networks through the shown path 2A with a case role management system 1016, which may be configured by user location configuration interface 1014. As process 1000 further shows, case role management system 1016, after receiving a confirmed case role request responds over one or more networks via path 2B to a handheld device.

Process flow 1000 then proceeds to role assumption step 1008. Role assumption step 1008 accepts confirmation of a successful role assumption or role-handoff and updates the graphical user interface accordingly. As shown by process 1000, role assumption step 1008 can, for example, transition the graphical user interface to presenting a case information interface at patient treatment interface step 1010. Patient treatment interface step 1010 presents further details about the case for which the user of a handheld device now holds an assumed role. Among other things, this interface facilitates retrieval and real-time management of case information. In some embodiments, case role management system 1016 is further capable of logging the time corresponding to a role assumption or role-handoff. Recording such timestamps enables medical professionals associated with the case to determine all medical professionals who were and are currently involved with a case. This information can also be used to generate appropriate invoices and billing reports for a medical practice. In certain implementations, appropriate medical professionals may be notified, such as by a case alert, based on predefined event triggers or rules maintained by a medical information management system.

FIG. 11 illustrates an example case summary interface 1100 for summarizing case details and facilitating role-handoffs. Case details may include details about a patient such as identifying information, medical history, and past and ongoing medical events corresponding to a medical procedure being conducted on the identified patient. The case summary interface 1100 also facilitates the assumption of roles by medical professionals or role-handoffs between medical professionals. Thus, for example, the shown case summary interface 1100 may implement the process flow 1000 for assuming roles and conducting role-handoffs. In particular implementations, case summary interface 1100 may be presented when a user selection of a particular patient tracking entry corresponding to a case is received at a graphical case board interface and the user does not already have a role associated with the case.

As shown in the illustrated embodiment, case summary interface 1100 includes case summary tabs 1102 and a case details list 1104. These components of case summary interface 1100 facilitate quick data review of a case and also enable assumption of roles and role-handoffs. As shown, case summary tabs 1102 include a number of tabs for interacting with case summary interface 1100. For example, as shown, a contextual return tab may receive a user selection to return to a graphical case board interface. In addition, other shown tabs such as the preparation or assist tab, the supervise or direct tab, and the provide care tab may receive selections through a user interface for assuming a role or handing-off roles between medical professionals. Case details list 1104 displays specific information corresponding to the case in list form, including patient information and medical history. Case details list 1104 may also present a sequence of medical events corresponding to events that have occurred with respect to a case and any other informational items relevant to the case.

While case summary interface 1100 is demonstrated as including specific components and displaying particular information, it should be understood that various embodiments may operate using any suitable arrangement and collection of components having any appropriate display format and such arrangements and components may be configurable by a particular medical practice or anesthesia care location.

Although the present disclosure describes several embodiments, it should be understood that a myriad of changes, substitutions, and alterations can be made without departing from the spirit and scope of the invention as defined by the appended claims.

What is claimed is:

1. A handheld apparatus comprising:
a user interface comprising a display and capable of receiving user input;
a wireless network interface capable of coupling to a central medical information management system;
a memory maintaining a medical information management application;
a processor operable, when executing the medical information management application:
to communicate a practice key identifying a selected one of a plurality of medical practices to the medical information management system;
to receive a list of authorized users for the selected medical practice from the medical information management system;
to display the list using the display;
to receive a selection of one of the authorized users using the user interface;
to receive a password associated with the selected authorized user using the user interface;
to communicate an identification of the selected authorized user and the password to the medical information management system;
to receive a quick access code associated with the selected authorized user from the medical information management system;
to receive electronic medical case information corresponding to the selected medical practice from the medical information management system;
to provide a use mode and a standby mode, wherein the use mode permits access to the electronic medical case information and the standby mode restricts access to the electronic medical case information; and
to permit transition from the standby mode to the use mode based on entry of the quick access code using the user interface.

2. The apparatus of claim 1, wherein the standby mode is a selected one of an exiting of the medical information management application or a state entered after a period of inactivity.

3. The apparatus of claim 1, wherein the processor is further operable, when executing the medical information management application, to:
receive a list of practice locations;
communicate a selected one of the practice locations to the medical information management system; and
receive electronic medical case information corresponding to the selected medical practice and practice location from the medical information management system.

4. The apparatus of claim 1, wherein the processor is further operable, when executing the medical information management application, to:
receive a selection of one of the cases in the received electronic medical case board information;
receive a selection of one of a plurality of case roles for the selected case;
communicate an identification of the selected authorized user and the selected case role to the medical information management system;
receive an update to the electronic medical case information, the update including, an association of the selected user to the selected case role.

5. The apparatus of claim 1, wherein the password has a minimum length of at least six characters, and the quick access code has a minimum length less than that for the password and uses a reduced character set.

6. The apparatus of claim 3, wherein the processor is further operable, when executing the medical information management application, to display the electronic medical case information using the display, wherein displaying comprises visually emphasizing and sorting the electronic medical case information based on an affiliation with the selected authorized user.

7. The apparatus of claim 3, wherein the processor is further operable, when executing the medical information management application, to:
display the electronic medical case information using the display;
receive a selection of one of the cases in the electronic medical case information using the user interface; and
provide a patient treatment interface for the selected case based on whether the selected authorized user has an affiliation with the selected case.

8. A method comprising:
communicating a practice key identifying a selected one of a plurality of medical practices to a medical information management system;
receiving a list of authorized users for the selected medical practice from the medical information management system;
displaying the list using a display;
receiving a selection of one of the authorized users using a user interface;
receiving a password associated with the selected authorized user using the user interface;
communicating an identification of the selected authorized user and the password to the medical information management system;
receiving a quick access code associated with the selected authorized user from the medical information management system;
receiving electronic medical case information corresponding to the selected medical practice from the medical information management system;
providing a use mode and a standby mode, wherein the use mode permits access to the electronic medical case information and the standby mode restricts access to the electronic medical case information; and
permitting transition from the standby mode to the use mode based on entry of the quick access code using the user interface.

9. The method of claim 8, wherein the standby mode is a selected one of an exiting of the medical information management application or as state entered after a period of inactivity.

10. The method of claim 8, further comprising:
receiving a list of practice locations;
communicating a selected one of the practice locations to the medical information management system; and
receiving electronic medical case information corresponding to the selected medical practice and practice location from the medical information management system.

11. The method of claim 8, further comprising:
receiving a selection of one of the cases in the received electronic medical case board information;
receiving a selection of one of a plurality of case roles for the selected case;
communicating an identification of the selected authorized user and the selected case role to the medical information management system;
receiving an update to the electronic medical case information, the update including an association of the selected user to the selected case role.

12. The method of claim 8, wherein the password has a minimum length of at least six characters, and the quick access code has a minimum length less than that for the password and uses a reduced character set.

13. The method of claim 10, further comprising displaying the electronic medical case information using the display, wherein displaying comprises visually emphasizing and sorting the electronic medical case information based on an affiliation with the selected authorized user.

14. The method of claim 10, further comprising:
displaying the electronic medical case information using the display;
receiving a selection of one of the cases in the electronic medical case information using the user interface; and
providing a patient treatment interface for the selected case based on whether the selected authorized user has an affiliation with the selected case.

15. A system, comprising;
a central medical information management system;
one or more medical information management applications each residing on a wireless handheld device and operable, when executed, to:
communicate a practice key identifying a selected one of a plurality of medical practices to the medical information management system;
receive a list of authorized users for the selected medical practice from the medical information management system;
display the list using a display;
receive a selection of one of the authorized users using a user interface;
receive a password associated with the selected authorize user using the user interface;
communicate an identification of the selected authorized user and the password to the medical information management system;
receive a quick access code associated with the selected authorized user from the medical information management system;
receive electronic medical case information corresponding to the selected medical practice from the medical information management system;
provide a use mode and a standby mode, wherein the use mode permits access to the electronic medical case information and the standby mode restricts access to the electronic medical case information; and
permit transition from the standby mode to the use mode based on entry of the quick access code using the user interface.

16. The system of claim 15, wherein the standby mode is a selected one of an exiting of the medical information management application or a state entered after a period of inactivity.

17. The system of claim 15, wherein the one or more medical information management applications are further operable, when executed, to:
receive a list of practice locations;
communicate a selected one of the practice locations to the medical information management system; and
receive electronic medical case information corresponding to the selected medical practice and practice location from the medical information management system.

18. The system of claim 15, wherein the one or more medical information management applications are further operable, when executed, to;
receive a selection of one of the cases in the received electronic medical case board information;
receive a selection of one of a plurality of case roles for the selected case;
communicate an identification of the selected authorized user and the selected case role to the medical information management system;
receive an update to the electronic medical case information, the update including an association of the selected user to the selected case role.

19. The system of claim 15, wherein the password has a minimum length of at least six characters, and the quick access code has a minimum length less than that for the password and uses a reduced character set.

20. The system of claim 17, wherein the one or more medical information management applications are further operable, when executed, to display the electronic medical case information using the display, wherein displaying comprises visually emphasizing and sorting the electronic medical case information based on an affiliation with the selected authorized user.

21. The system of claim 17, wherein the one or more medical information management applications are further operable, when executed, to:
   display the electronic medical case information using the display;
   receive a selection of one of the cases in the electronic medical case information using the user interface; and
   provide a patient treatment interface for the selected case based on whether the selected authorized user has an affiliation with the selected case.

\* \* \* \* \*